(12) United States Patent
Yoshioka et al.

(10) Patent No.: US 11,785,843 B2
(45) Date of Patent: Oct. 10, 2023

(54) PHOTOELECTRIC CONVERSION ELEMENT, OPTICAL SENSOR, AND IMAGING ELEMENT

(71) Applicant: FUJIFILM Corporation, Tokyo (JP)

(72) Inventors: Tomoaki Yoshioka, Kanagawa (JP); Eiji Fukuzaki, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 514 days.

(21) Appl. No.: 16/812,378

(22) Filed: Mar. 9, 2020

(65) Prior Publication Data

US 2020/0212107 A1 Jul. 2, 2020

Related U.S. Application Data

(63) Continuation of application No. PCT/JP2018/033429, filed on Sep. 10, 2018.

(30) Foreign Application Priority Data

Sep. 14, 2017 (JP) ................................. 2017-176795

(51) Int. Cl.
*C07D 333/50* (2006.01)
*H01L 27/146* (2006.01)
*H10K 85/60* (2023.01)
*H01L 31/0392* (2006.01)
*H10K 39/00* (2023.01)

(52) U.S. Cl.
CPC ....... *H10K 85/6572* (2023.02); *C07D 333/50* (2013.01); *H10K 85/622* (2023.02); *H01L 31/03926* (2013.01); *H10K 39/00* (2023.02)

(58) Field of Classification Search
CPC ................ C07D 333/50; Y02E 10/549; H10K 85/6572; H10K 85/622; H10K 85/654; H10K 85/631; H10K 85/615; H10K 85/211; H10K 39/00; H10K 30/30; H10K 30/00; H01L 31/03926; H01L 27/146; Y02P 70/50
See application file for complete search history.

(56) References Cited

U.S. PATENT DOCUMENTS

| | | | |
|---|---|---|---|
| 4,500,622 A | 2/1985 | Horie et al. | |
| 9,349,965 B2 | 5/2016 | Yofu et al. | |
| 2016/0155975 A1 | 6/2016 | Jin et al. | |
| 2020/0403163 A1* | 12/2020 | Yoshioka | ............ H01L 51/0059 |

FOREIGN PATENT DOCUMENTS

| | | | |
|---|---|---|---|
| JP | S57147656 | | 9/1982 |
| JP | 2012033443 | | 2/2012 |
| JP | 20120334433 | * | 2/2012 |
| JP | 2012077064 | | 4/2012 |
| JP | 2015189679 | | 11/2015 |
| KR | 20140082569 | | 7/2014 |

OTHER PUBLICATIONS

JP20120334433—machine-translation, machine translation of JP 20120334433.*
"International Search Report (Form PCT/ISA/210) of PCT/JP2018/033429," dated Oct. 9, 2018, with English translation thereof, pp. 1-5.
"Written Opinion of the International Searching Authority (Form PCT/ISA/237) of PCT/JP2018/033429," dated Oct. 9, 2018, with English translation thereof, pp. 1-7.

* cited by examiner

*Primary Examiner* — Sun Jae Yoo
(74) *Attorney, Agent, or Firm* — JCIPRNET

(57) ABSTRACT

An object of the invention is to provide a photoelectric conversion element exhibiting an excellent production suitability.
Also, the other object of the invention is to provide an optical sensor and an imaging element comprising the photoelectric conversion element.
The photoelectric conversion element of the invention includes a conductive film, a photoelectric conversion film, and a transparent conductive film, in this order, in which the photoelectric conversion film contains a compound represented by Formula (1) below.

20 Claims, 4 Drawing Sheets

PHOTOELECTRIC CONVERSION ELEMENT, OPTICAL SENSOR, AND IMAGING ELEMENT

CROSS-REFERENCE TO RELATED APPLICATIONS

This application is a Continuation of PCT International Application No. PCT/JP2018/033429 filed on Sep. 10, 2018, which claims priority under 35 U.S.C. § 119(a) to Japanese Patent Application No. 2017-176795 filed on Sep. 14, 2017. The above application is hereby expressly incorporated by reference, in its entirety, into the present application.

BACKGROUND OF THE INVENTION

1. Field of the Invention

The present invention relates to a photoelectric conversion element, an optical sensor, and an imaging element.

2. Description of the Related Art

In the related art, a planar solid-state imaging element in which photodiodes (PDs) are two-dimensionally arranged and a signal charge generated in each PD is read out by a circuit is widely used as a solid-state imaging element.

In order to realize a color solid-state imaging element, a structure in which a color filter transmitting light of a specific wavelength is disposed on a light incident surface side of the planar solid-state imaging element is generally used. Currently, a single plate solid-state imaging element in which the color filter transmitting blue (B) light, green (G) light, and red (R) light is regularly arranged on each PD which is two-dimensionally arranged is well known. However, in this single plate solid-state imaging element, light which is not transmitted through the color filter is not used, thus light utilization efficiency is poor.

In order to solve these disadvantages, in recent years, development of a photoelectric conversion element having a structure in which an organic photoelectric conversion film is disposed on a substrate for reading out a signal has progressed.

For example, Example of JP2012-077064A discloses a photoelectric conversion element having a photoelectric conversion film containing following compounds.

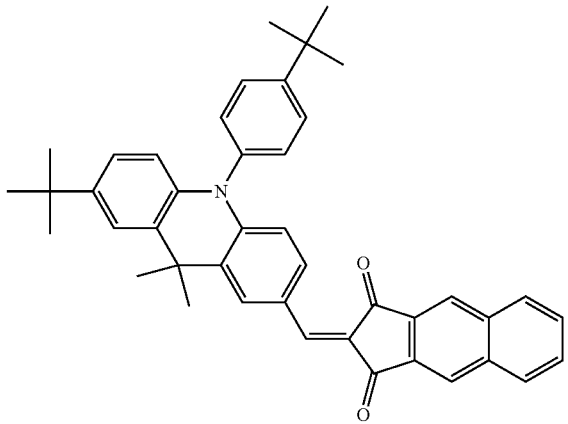 [SMILES: CC(C)(C)c1ccc(N2c3ccc(C=C4C(=O)c5cc6ccccc6cc5C4=O)cc3C(C)(C)c3cc(C(C)(C)C)ccc32)cc1]

SUMMARY OF THE INVENTION

The present inventors have produced and examined the photoelectric conversion element containing the compound in the photoelectric conversion film disclosed in JP2012-077064A, and found that the photoelectric conversion film containing the compound is easily affected by a temperature of a substrate (hereinafter, also referred to as a "substrate temperature") in a case where the photoelectric conversion film is formed on the substrate by a vapor deposition method. Specifically, it has been found that the obtained photoelectric conversion element may have a larger dark current depending on the substrate temperature during vapor deposition and may not satisfy the recently required level.

Stated another way, it has been clarified that the production suitability of the photoelectric conversion element needs to be improved by further improving the dependency of the photoelectric conversion film on the substrate temperature during vapor deposition.

An object of the invention is to provide a photoelectric conversion element exhibiting an excellent production suitability.

Another object of the invention is to provide an optical sensor and an imaging element including the photoelectric conversion element.

As a result of intensive studies to achieve the above problems, the present inventors have found that the above problems can be solved by a photoelectric conversion element having a photoelectric conversion film containing a compound represented by Formula (1), and completed the invention.

Stated another way, it has been found that the above problems by the following configuration.

[1] A photoelectric conversion element comprising a conductive film, a photoelectric conversion film, and a transparent conductive film, in this order, in which the photoelectric conversion film contains a compound represented by Formula (1) below.

[2] The photoelectric conversion element according to [1], in which the compound represented by Formula (1) is a compound represented by Formula (2) below.

[3] The photoelectric conversion element according to [2], in which the compound represented by Formula (2) is a compound represented by Formula (3) below.

[4] The photoelectric conversion element according to [3], in which the compound represented by Formula (3) is a compound represented by Formula (4) below.

[5] The photoelectric conversion element according to any one of [1] to [4], in which the $R^4$ and the $R^5$ are alkyl groups which may have a substituent, or the $R^4$ and $R^5$ bond to each other to form an alicyclic hydrocarbon ring which may have a substituent.

[6] The photoelectric conversion element according to any one of [1] to [5], in which the photoelectric conversion film further contains an n-type organic semiconductor and has a bulk hetero structure formed in a state where the compound represented by Formula (1) described above and the n-type organic semiconductor are mixed.

[7] The photoelectric conversion element according to any one of [1] to [6], further comprising one or more interlayers between the conductive film and the transparent conductive film, in addition to the photoelectric conversion film.

[8] An optical sensor comprising the photoelectric conversion element according to any one of [1] to [7].

[9] An imaging element comprising the photoelectric conversion element according to any one of [1] to [7].

According to the invention, it is possible to provide a photoelectric conversion element exhibiting an excellent production suitability.

According to the invention, it is possible to provide an optical sensor and an imaging element including the photoelectric conversion element.

DESCRIPTION OF THE PREFERRED EMBODIMENTS

Hereinafter, the invention will be described in detail.

The description of the constituent elements described below may be made based on typical embodiments of the invention, but the present invention is not limited to such embodiments.

In addition, in the present specification, the numerical range represented by "to" means a range including numerical values denoted before and after "to" as a lower limit value and an upper limit value.

Photoelectric Conversion Element

A feature of the invention compared to the related art is that a compound represented by Formula (1) described below (hereinafter also referred to as a "specific compound") is used for a photoelectric conversion film.

The present inventors have found that the compound contained in the photoelectric conversion film in the related art is more easily crystallized on the substrate as the substrate temperature during vapor deposition performed for forming the photoelectric conversion film. Stated another way, it is assumed that, in the obtained photoelectric conversion film, the compound in the photoelectric conversion film is crystallized depending on the substrate temperature during vapor deposition, and as a result, the dark current of the obtained photoelectric conversion element becomes large.

On the other hand, the specific compound is difficult to be crystallized because $R^1$ is a predetermined organic group, that is, has a low dependency on the substrate temperature during vapor deposition of the photoelectric conversion film. For this reason, the obtained photoelectric conversion element is suppressed in the dark current due to the substrate temperature during vapor deposition performed for forming the photoelectric conversion film, and is excellent in the production suitability.

Further, the present inventors have confirmed that, in the photoelectric conversion element including the photoelectric conversion film containing the specific compound, even in a case where the composition ratio of the compound in the photoelectric conversion film (the content of the compound in the photoelectric conversion film) varies, the photoelectric conversion efficiency (the external quantum efficiency) does not fluctuate greatly. Stated another way, the photoelectric conversion element containing the photoelectric conversion film containing the specific compound is excellent in the production suitability since the photoelectric conversion efficiency has a low dependency on the composition ratio.

Figure 1A:
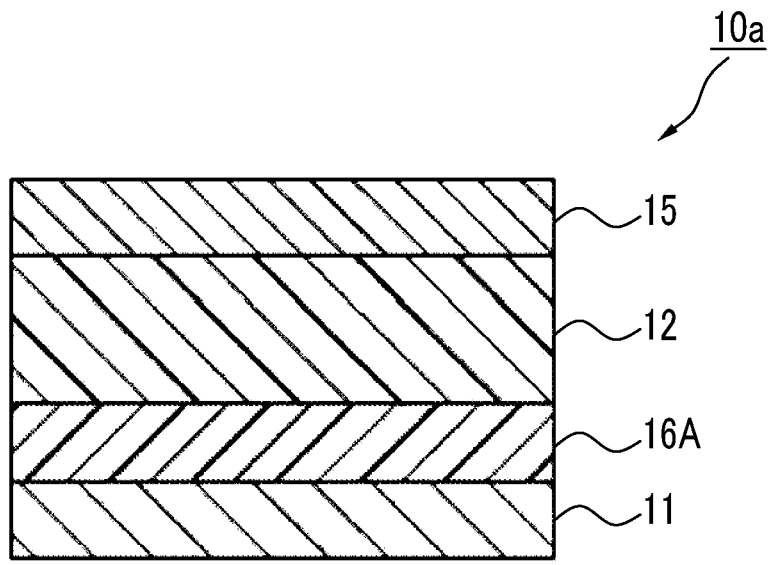
FIG. 1A is a schematic cross-sectional view showing an example of a configuration of a photoelectric conversion element.
Figure 1B:
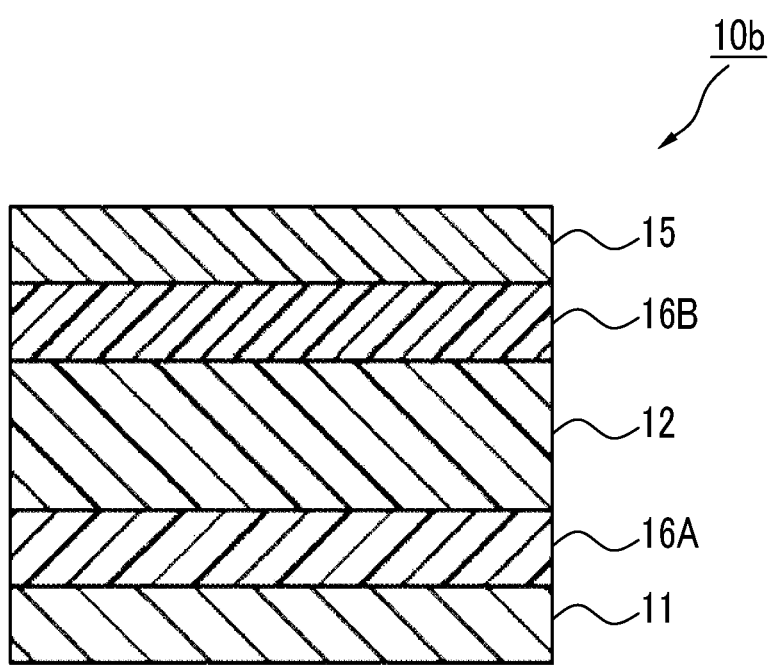
FIG. 1B is a schematic cross-sectional view showing an example of a configuration of a photoelectric conversion element.

Hereinafter, preferred embodiments of a photoelectric conversion element of the invention will be described with reference to the drawings. FIGS. 1A and 1B show schematic cross-sectional views of one embodiment of a photoelectric conversion element of the invention.

A photoelectric conversion element 10a shown in FIG. 1A has a configuration in which a conductive film (hereinafter, also referred to as a lower electrode) 11 functioning as the lower electrode, an electron blocking film 16A, a photoelectric conversion film 12 containing the specific compound described below, and a transparent conductive film (hereinafter, also referred to as an upper electrode) 15 functioning as the upper electrode are laminated in this order.

FIG. 1B shows a configuration example of another photoelectric conversion element. A photoelectric conversion element 10b shown in FIG. 1B has a configuration in which the electron blocking film 16A, the photoelectric conversion film 12, a positive hole blocking film 16B, and the upper electrode 15 are laminated on the lower electrode 11 in this order. The lamination order of the electron blocking film 16A, the photoelectric conversion film 12, and the positive hole blocking film 16B in FIGS. 1A and 1B may be appropriately changed according to the application and the characteristics.

In the photoelectric conversion element 10a (or 10b), it is preferable that light is incident on the photoelectric conversion film 12 through the upper electrode 15.

In a case where the photoelectric conversion element 10a (or 10b) is used, the voltage can be applied. In this case, it is preferable that the lower electrode 11 and the upper electrode 15 form a pair of electrodes and the voltage of $1 \times 10^{-5}$ to $1 \times 10^7$ V/cm is applied thereto. From the viewpoint of performance and power consumption, the voltage to be applied is more preferably $1 \times 10^{-4}$ to $1 \times 10^7$ V/cm, and still more preferably $1 \times 10^{-3}$ to $5 \times 10^6$ V/cm.

The voltage application method is preferable that the voltage is applied such that the electron blocking film 16A side is a cathode and the photoelectric conversion film 12 side is an anode, in FIGS. 1A and 1B. In a case where the photoelectric conversion element 10a (or 10b) is used as an optical sensor, or also in a case where the photoelectric conversion element 10a (or 10b) is incorporated in an imaging element, the voltage can be applied by the same method.

As described in detail below, the photoelectric conversion element 10a (or 10b) can be suitably applied to applications of the optical sensor and the imaging element.

Figure 2:
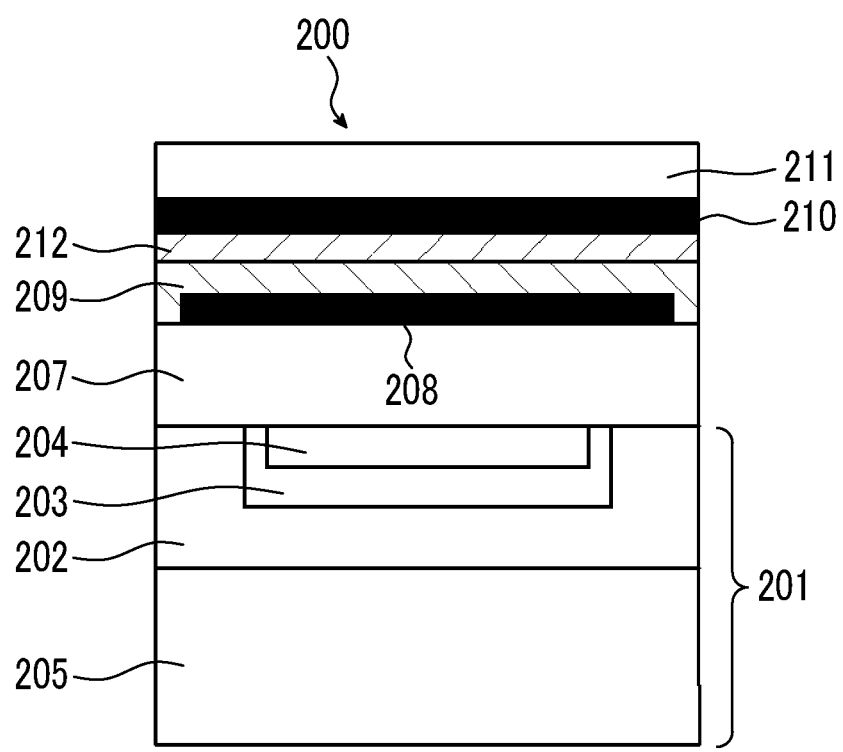
FIG. 2 is a schematic cross-sectional view of one pixel of a hybrid type photoelectric conversion element.

In addition, a schematic cross-sectional view of another embodiment of a photoelectric conversion element of the invention is shown in FIG. 2.

The photoelectric conversion element 200 shown in FIG. 2 is a hybrid type photoelectric conversion element comprising an organic photoelectric conversion film 209 and an inorganic photoelectric conversion film 201. The organic photoelectric conversion film 209 contains the specific compound described below.

The inorganic photoelectric conversion film 201 has an n-type well 202, a p-type well 203, and an n-type well 204 on a p-type silicon substrate 205.

Blue light is photoelectrically converted (a B pixel) at a p-n junction formed between the p-type well 203 and the n-type well 204, and red light is photoelectrically converted (an R pixel) at a p-n junction formed between the p-type well 203 and the n-type well 202. The conduction types of the n-type well 202, the p-type well 203, and the n-type well 204 are not limited thereto.

Furthermore, a transparent insulating layer 207 is disposed on the inorganic photoelectric conversion film 201.

A transparent pixel electrode 208 divided for each pixel is disposed on the insulating layer 207. The organic photoelectric conversion film 209 which absorbs green light and performs photoelectric conversion is disposed on the transparent pixel electrode in a single layer configuration commonly for each pixel. The electron blocking film 212 is disposed on the organic photoelectric conversion film in a single layer configuration commonly for each pixel. A transparent common electrode 210 with a single layer configuration is disposed on the electron blocking film. A transparent protective film 211 is disposed on the uppermost layer. The lamination order of the electron blocking film 212 and the organic photoelectric conversion film 209 may be reversed from that in FIG. 2, and the common electrode 210 may be disposed so as to be divided for each pixel.

The organic photoelectric conversion film 209 constitutes a G pixel for detecting green light.

The pixel electrode 208 is the same as the lower electrode 11 of the photoelectric conversion element 10a shown in FIG. 1A. The common electrode 210 is the same as the upper electrode 15 of the photoelectric conversion element 10a shown in FIG. 1A.

In a case where light from a subject is incident on the photoelectric conversion element 200, green light in the incident light is absorbed by the organic photoelectric conversion film 209 to generate optical charges. The optical charges flow into and accumulate in a green signal charge accumulation region not shown in the drawing from the pixel electrode 208.

Mixed light of the blue light and the red light transmitted through the organic photoelectric conversion film 209 enters the inorganic photoelectric conversion film 201. The blue light having a short wavelength is photoelectrically converted mainly at a shallow portion (in the vicinity of the p-n junction formed between the p-type well 203 and the n-type well 204) of a semiconductor substrate (the inorganic photoelectric conversion film) 201 to generate optical charges, and a signal is output to the outside. The red light having a long wavelength is photoelectrically converted mainly at a deep portion (in the vicinity of the p-n junction formed between the p-type well 203 and the n-type well 202) of the semiconductor substrate (the inorganic photoelectric conversion film) 201 to generate optical charges, and a signal is output to the outside.

In a case where the photoelectric conversion element 200 is used in the imaging element, a signal readout circuit (an electric charge transfer path in a case of a charge coupled device (CCD) type, or a metal-oxide-semiconductor (MOS) transistor circuit in a case of a complementary metal oxide semiconductor (CMOS) type), or the green signal charge accumulation region is formed in a surface portion of the p-type silicon substrate 205. In addition, the pixel electrode 208 is connected to the corresponding green signal charge accumulation region through vertical wiring.

Photoelectric Conversion Film

Specific Compound

The photoelectric conversion film 12 (or the organic photoelectric conversion film 209) is a film containing a specific compound (the compound represented by Formula (1)) as the photoelectric conversion material. The photoelectric conversion element excellent in the production suitability can be obtained by using the compound.

Hereinafter, the specific compound (the compound represented by Formula (1)) will be described.

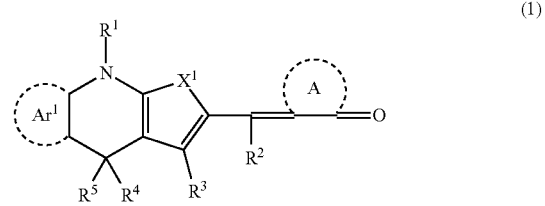

(1)

In Formula (1), $R^1$ represents an alkyl group which may have a substituent.

The number of carbon atoms of the alkyl group represented by $R^1$ is not particularly limited, but is preferably 1 to 15, more preferably 1 to 10, and still more preferably 1 to 6. The alkyl group may be linear, branched, or cyclic.

Examples of the alkyl group include a methyl group, an ethyl group, an n-propyl group, an i-propyl group, an n-butyl group, a t-butyl group, an n-hexyl group, a cyclopentyl group, and a cyclohexyl group.

A substituent which may be included in an alkyl group is not particularly limited, but for example, a substituent W described below is exemplified, and an aryl group (preferably having 6 to 18 carbon atoms, and more preferably having 6 carbon atoms), a heteroaryl group (preferably having 5 to 18 carbon atoms, and more preferably having 5 to 6 carbon atoms), or a halogen atom (preferably a fluorine atom or a chlorine atom) is preferable.

$R^2$ and $R^3$ each independently represent a hydrogen atom or a substituent.

A substituent represented by $R^2$ and $R^3$ is not particularly limited, but for example, a substituent W described below is exemplified and a methyl group is preferable.

$R^2$ and $R^3$ are preferably hydrogen atoms.

$R^4$ and $R^5$ each independently represent a hydrogen atom or a substituent.

The substituent represented by $R^4$ and $R^5$ is not particularly limited and examples thereof include a substituent W described below. Among these, the substituent represented by $R^4$ and $R^5$ is preferably an alkyl group, an aryl group, or a heteroaryl group.

An alkyl group represented by $R^4$ and $R^5$ may be linear, branched, or cyclic, and the number of carbon atoms is preferably 1 to 10, more preferably 1 to 6, and still more preferably 1 to 3. Examples of the alkyl group represented by $R^4$ and $R^5$ include, specifically, a methyl group, an ethyl group, an n-propyl group, an i-propyl group, an n-butyl group, a t-butyl group, an n-hexyl group, a cyclopentyl group, and a cyclohexyl group.

The number of carbon atoms of the aryl group represented by $R^4$ and $R^5$ is not particularly limited, but is preferably 6 to 30, more preferably 6 to 18, and still more preferably 6. The aryl group may have a monocyclic structure or a condensed ring structure (a fused ring structure) in which two or more rings are condensed.

As an aryl group, for example, a phenyl group, a naphthyl group, or an anthryl group is preferable, and a phenyl group is more preferable.

The number of carbon atoms of the heteroaryl group (monovalent aromatic heterocyclic group) represented by $R^4$ and $R^5$ is not particularly limited, but is preferably 3 to 18, and more preferably 3 to 5.

Examples of the hetero atom included in a heteroaryl group include a sulfur atom, an oxygen atom, a nitrogen atom, a selenium atom, a tellurium atom, a phosphorus atom, a silicon atom, a boron atom, and the like, and a sulfur atom, an oxygen atom, or a nitrogen atom is preferable.

The number of hetero atoms contained in the heteroaryl group is not particularly limited, but is preferably 1 to 10, more preferably 1 to 4, and still more preferably 1 to 2.

The number of ring members of the heteroaryl group is not particularly limited, but is preferably 3 to 8, more preferably 5 to 7, and still more preferably 5 to 6. The heteroaryl group may have a monocyclic structure or a condensed ring structure in which two or more rings are condensed. In a case of the condensed ring structure, an aromatic hydrocarbon ring having no hetero atom (for example, a benzene ring) may be included.

Examples of the heteroaryl group include a furyl group, a pyridyl group, a quinolyl group, an isoquinolyl group, an acridinyl group, a phenanthridinyl group, a pteridinyl group, a pyrazinyl group, a quinoxalinyl group, a pyrimidinyl group, a quinazolyl group, a pyridazinyl group, a cinnolinyl group, a phthalazinyl group, a triazinyl group, an oxazolyl group, a benzoxazolyl group, a thiazolyl group, a benzothiazolyl group, an imidazolyl group, a benzimidazolyl group, a pyrazolyl group, an indazolyl group, an isoxazolyl group, a benzisoxazolyl group, an isothiazolyl group, a benzisothiazolyl group, an oxadiazolyl group, a thiadiazolyl group, a triazolyl group, a tetrazolyl group, a benzofuryl group, a thienyl group, a benzothienyl group, a dibenzofuryl group, a dibenzothienyl group, a pyrrolyl group, an indolyl group, an imidazopyridinyl group, and a carbazolyl group.

An alkyl group represented by $R^4$ and $R^5$, an aryl group represented by $R^4$ and $R^5$, and a heteroaryl group represented by $R^4$ and $R^5$ may further have a substituent. Examples of the substituents include a substituent W described below.

$R^4$ and $R^5$ may bond to each other to form a ring. Examples of the ring include an aromatic hydrocarbon ring, an alicyclic hydrocarbon ring, an aromatic heterocyclic ring, an alicyclic heterocyclic ring, and a polycyclic fused ring formed by combining two or more of these rings. Examples of the ring include a 3- to 10-membered ring, and a 4- to 8-membered ring is preferable, and a 5- or 6-membered ring is more preferable.

Among these, as the ring, an alicyclic hydrocarbon ring is preferable, and a cyclohexane ring and a cyclopentane ring are exemplified.

The ring may further have a substituent. Examples of the substituents include a substituent W described below.

Among these, it is preferable that $R^4$ and $R^5$ are alkyl groups which may have a substituent or bond to each other to form an alicyclic hydrocarbon ring which may have a substituent from the viewpoint that the dependency on the substrate temperature during vapor deposition becomes smaller and the dependency of photoelectric conversion efficiency on the composition ratio of the becomes smaller.

$X^1$ represents a sulfur atom or $-R^{a1}C=CR^{a2}-$.

$R^{a1}$ and $R^{a2}$ each independently represent a hydrogen atom or a substituent.

The substituent represented by $R^{a1}$ and $R^{a2}$ is not particularly limited, but a substituent W described below is exemplified. As the substituent represented by $R^{a1}$ and $R^{a2}$, an alkyl group (which may be linear, branched, or cyclic and preferably has 1 to 10 carbon atoms and more preferably has 1 to 6 carbon atoms), an aryl group (preferably having 6 to 18 carbon atoms and more preferably having 6 carbon atoms), or a heteroaryl group (preferably having 5 to 18 carbon atoms and more preferably having 5 to 6 carbon atoms) is preferable, and among these, a methyl group is more preferable.

$R^{a1}$ and $R^{a2}$ are preferably hydrogen atoms.

$Ar^1$ represents a monocyclic aromatic ring containing at least two carbon atoms, which may have a substituent. In addition, two carbon atoms intend two adjacent carbon atoms in the ring containing a nitrogen atom specified in Formula (1) and both carbon atoms are the atom constituting $Ar^1$.

A monocyclic aromatic ring represented by $Ar^1$ may be any of a monocyclic aromatic hydrocarbon ring (monocyclic aryl ring) and a monocyclic aromatic heterocyclic ring (monocyclic heteroaryl ring).

The monocyclic aromatic hydrocarbon ring represented by AP is not particularly limited, but a 3- to 10-membered ring is exemplified, among these, a 4- to 8-membered ring is preferable, and a 5- or 6-membered ring is more preferable.

The monocyclic aromatic heterocyclic ring represented by $Ar^1$ is not particularly limited, but a 3- to 8-membered ring is exemplified, among these, a 5- to 7-membered ring is preferable, and a 5- or 6-membered ring is more preferable.

Examples of the hetero atom included in the monocyclic aromatic heterocyclic ring represented by $Ar^1$ include a sulfur atom, an oxygen atom, a nitrogen atom, a selenium atom, a tellurium atom, a phosphorus atom, a silicon atom, a boron atom, and the like, and a sulfur atom, an oxygen atom, or a nitrogen atom is preferable.

The number of the hetero atoms included in the monocyclic aromatic heterocyclic ring represented by $Ar^1$ is not particularly limited, but preferably 1 to 4, and more preferably 1 to 2.

$Ar^1$ may have a substituent. The substituent is not particularly limited, for example, a substituent W described below is exemplified. As the substituent, any of a halogen atom (preferably a chlorine atom), an alkyl group (which may be linear, branched, or cyclic and preferably has 1 to 10 carbon atoms and more preferably has 1 to 6 carbon atoms), an aryl group (preferably having 6 to 18 carbon atoms and more preferably having 6 carbon atoms), or a heteroaryl group (preferably having 5 to 18 carbon atoms and more preferably having 5 to 6 carbon atoms), or a silyl group (which may be any of linear, branched, or cyclic and preferably has 1 to 4 of silicon numbers and more preferably has 1 of silicon numbers) is preferable.

The plurality of substituents on $Ar^1$ may bond to each other to form a ring. However, in a case where a plurality of the substituents bond to each other on the $Ar^1$ to form a ring, the ring does not include an aromatic ring. Stated another way, the ring formed by bonding of the plurality of substituents on $Ar^1$ forms the fused ring structure with $Ar^1$, but in the fused ring structure, an aromatic ring is only $Ar^1$.

Examples of the ring formed by bonding of a plurality of substituents on $Ar^1$ include an alicyclic hydrocarbon ring, an alicyclic heterocyclic ring, and a polycyclic fused ring formed by combining two or more of these rings. As the ring, a 3- to 10-membered ring is preferable, and a 4- to 8-membered ring is more preferable, and a 5- or 6-membered ring is still more preferable.

Among these, as the ring, an alicyclic hydrocarbon ring or an alicyclic heterocyclic ring is preferable, and for example, a cyclohexane ring and a cyclopentane ring which may contain a hetero atom such as a sulfur atom, an oxygen atom, or a nitrogen atom.

The ring may further have a substituent. Examples of the substituents include a substituent W described below.

A represents a ring containing at least two carbon atoms. The two carbon atoms refer to a carbon atom in a carbonyl group specified in Formula (1) and a carbon atom, specified in Formula (1), adjacent to the carbon atom in the carbonyl group, and both the carbon atoms are atoms constituting A. In the ring, the carbon atom constituting the ring may be substituted with another carbonyl carbon (>C=O) or thiocarbonyl carbon (>C=S).

In addition, another carbonyl carbon (>C=O) here means a carbonyl carbon that a carbon atom constituting the ring has in addition to the carbonyl carbon specified in Formula (1).

The number of carbon atoms of a ring of A is preferably 3 to 30, more preferably 3 to 20, and still more preferably 3 to 15. The above-described number of carbon atoms is a number containing two carbon atoms specified in the formula.

A may have a hetero atom, for example, a nitrogen atom, a sulfur atom, an oxygen atom, a selenium atom, a tellurium atom, a phosphorus atom, a silicon atom, and a boron atom are exemplified, and a nitrogen atom, a sulfur atom, or an oxygen atom is preferable, and an oxygen atom is more preferable.

A may have a substituent, and as the substituent, any of a halogen atom (preferably a chlorine atom), an alkyl group (which may be linear, branched, or cyclic and preferably has 1 to 10 carbon atoms and more preferably has 1 to 6 carbon atoms), an aryl group (preferably having 6 to 18 carbon atoms and more preferably having 6 carbon atoms), or a heteroaryl group (preferably having 5 to 18 carbon atoms and more preferably having 5 to 6 carbon atoms), or a silyl group (which may be any of linear, branched, or cyclic and preferably has 1 to 4 of silicon numbers and more preferably has 1 of silicon numbers) is preferable.

The number of hetero atoms in A is preferably 0 to 10, more preferably 0 to 5, and still more preferably 0 to 2. The number of hetero atoms is the number of the hetero atoms (intended to include a carbonyl carbon specified in Formula (1)) introduced in the ring by substituting the carbon atom constituting the ring represented by A with a carbonyl carbon (>C=O) or a thiocarbonyl carbon (>C=S), and the number excluding the number of hetero atoms which included in the substituent of A.

A may or may not indicate aromaticity.

A may have a monocyclic structure or a condensed ring structure, but is preferably a 5-membered ring, a 6-membered ring, or a fused ring containing at least any one of a 5-membered ring or a 6-membered ring. The number of rings forming the fused ring is preferably 1 to 4, and more preferably 1 to 3.

The ring represented by A is preferably a substance normally used as an acidic nucleus with a merocyanine dye, and the specific examples thereof include the followings.

(a) 1,3-Dicarbonyl nucleus: for example, 1,3-indandione nucleus, 1,3-cyclohexanedione, 5,5-dimethyl-1,3-cyclohexanedione, 1,3-dioxane-4,6-dione, and the like.

(b) Pyrazolinone nucleus: for example, 1-phenyl-2-pyrazolin-5-one, 3-methyl-1-phenyl-2-pyrazolin-5-one, 1-(2-benzothiazolyl)-3-methyl-2-pyrazolin-5-one, and the like.

(c) Isoxazolinone nucleus: for example, 3-phenyl-2-isoxazolin-5-one, 3-methyl-2-isoxazolin-5-one, and the like.

(d) Oxindole nucleus: for example, 1-alkyl-2,3-dihydro-2-oxindole, and the like.

(e) 2,4,6-Trioxohexahydropyrimidine nucleus: for example, barbituric acid, 2-thiobarbituric acid and derivatives thereof, or the like. Examples of the derivative include a 1-alkyl form such as 1-methyl and 1-ethyl, a 1,3-dialkyl form such as 1,3-dimethyl, 1,3-diethyl, and 1,3-dibutyl, a 1,3-diaryl form such as 1,3-diphenyl, 1,3-di(p-chlorophenyl), 1,3-di(p-ethoxycarbonylphenyl), 1-alkyl-1-aryl form such as 1-ethyl-3-phenyl, and a 1,3-diheteroaryl form such as 1,3-di (2-pyridyl).

(f) 2-Thio-2,4-thiazolidinedione nucleus: for example, rhodanine and derivatives thereof. Examples of the derivatives include 3-alkylrhodanine such as 3-methylrhodanine, 3-ethylrhodanine, and 3-allylrhodanine, 3-arylrhodanine such as 3-phenylrhodanine, and 3-heteroaryl rhodanine such as 3-(2-pyridyl)rhodanine.

(g) 2-Thio-2,4-oxazolidinedione(2-thio-2,4-(3H, 5H)-oxazoledione nucleus: for example, 3-ethyl-2-thio-2,4-oxazolidinedione, and the like.

(h) Tianaphthenone nucleus: for example, 3(2H)-thianaphthenone-1,1-dioxide, and the like.

(i) 2-Thio-2,5-thiazolidinedione nucleus: for example, 3-ethyl-2-thio-2,5-thiazolidinedione, and the like.

(j) 2,4-Thiazolidinedione nucleus: for example, 2,4-thiazolidinedione, 3-ethyl-2,4-thiazolidinedione, 3-phenyl-2,4-thiazolidinedione, and the like.

(k) Thiazolin-4-one nucleus: for example, 4-thiazolinone, 2-ethyl-4-thiazolinone, and the like.

(l) 2,4-Imidazolidinedione (hydantoin) nucleus: for example, 2,4-imidazolidinedione, 3-ethyl-2,4-imidazolidinedione, and the like.

(m) 2-Thio-2,4-imidazolidinedione (2-thiohydantoin) nucleus: for example, 2-thio-2,4-imidazolidinedione, 3-ethyl-2-thio-2,4-imidazolidinedione, and the like.

(n) Imidazolin-5-one nucleus: for example, 2-propylmercapto-2-imidazolin-5-one, and the like.

(o) 3,5-Pyrazolidinedione nucleus: for example, 1,2-diphenyl-3,5-pyrazolidinedione, 1,2-dimethyl-3,5-pyrazolidinedione, and the like.

(p) Benzothiophene-3(2H)-one nucleus: for example, benzothiophene-3(2H)-one, oxobenzothiophene-3(2H)-one, dioxobenzothiophene-3(2H)-one, and the like.

(q) Indanone nucleus: for example, 1-indanone, 3-phenyl-1-indanone, 3-methyl-1-indanone, 3,3-diphenyl-1-indanone, 3,3-dimethyl-1-indanone, and the like.

(r) Benzofuran-3-(2H)-one nucleus: for example, benzofuran-3-(2H)-one, and the like.

(s) 2,2-Dihydrophenalene-1,3-dione nucleus, and the like.

In Formula (1), the respective substituents may bond to each other to form a ring. The respective substituents used herein refer to each of the substituents represented by $R^1$ to $R^5$, $R^{a1}$, and $R^{a2}$, and the substituents which may be included in A and $Ar^1$.

Specific embodiments in which the respective substituents bond to each other include a bond between $R^2$ and $R^3$, a bond between $R^3$ and $R^4$, a bond between $R^4$ and $R^5$, a bond between $R^{a1}$ and $R^{a2}$, a bond between substituents which may be included in $R^5$ and $Ar^1$, a bond between substituents which may be included in $Ar^1$, a bond between substituents which may $R^1$ and $Ar^1$, and a bond between substituents which may be included in A. However, as described above, in a case where a plurality of the substituents bond to each other on the $Ar^1$ to form a ring, the ring does not include an aromatic ring.

A compound represented by Formula (1) does not contain both an acidic group and a salt thereof. This is because these groups may cause decomposition of the compound during vapor deposition.

In the present specification, the "acidic group" is a substituent having a dissociative proton, and a substituent having a pKa of 11 or less is intended. The pKa of the acidic group is can be obtained according to the method "SMD/M05-2X/6-31G*" disclosed in J. Phys. Chem. A2011, 115, p. 6641 to 6645. Examples of the acidic group include acidic groups such as a carboxy group, a phosphonyl group, a phosphoryl group, a sulfo group, and a boric acid group, and groups having these acidic groups.

Also, Formula (1) includes all geometric isomers that can be distinguished based on the C=C double bond constituted by a carbon atom to which $R^2$ bonds and a carbon atom adjacent thereto in Formula (1). That is, both the cis isomer and the trans isomer which are distinguished based on the C=C double bond are included in Formula (1).

From the viewpoint of smaller dependency on the substrate temperature during vapor deposition and smaller dependency of the photoelectric conversion efficiency on the composition ratio, the specific compound is preferably a compound represented by Formula (2), among these, more preferably a compound represented by Formula (3) from the viewpoint of further smaller dependency on the substrate temperature during vapor deposition.

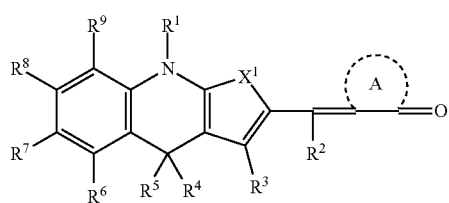

(2)

In Formula (2), $R^1$ to $R^5$, $X^1$, and A are the same as $R^1$ to $R^5$, $X^1$, and A in Formula (1), respectively, and the preferred embodiments are also the same.

$R^6$ to $R^9$ each independently represent a hydrogen atom or a substituent. Examples of the substituent represented by $R^6$ to $R^9$ include the same substituents that may be included in $Ar^1$.

$R^6$ to $R^9$ are each preferably a hydrogen atom or an aryl group which may have a substituent, from the viewpoint of smaller dependency on the substrate temperature during vapor deposition.

In Formula (2), respective substituents may bond to each other to form a ring. The respective substituents used herein refer to each of the substituents represented by $R^1$ to $R^9$, $R^{a1}$, and $R^{a2}$, and the substituents which may be included in A. Specific embodiments in which respective substituents bond to each other include a bond between $R^2$ and $R^3$, a bond between $R^3$ and $R^4$, a bond between $R^4$ and $R^5$, a bond between $R^5$ and $R^6$, a bond between $R^6$ and $R^7$, a bond between $R^7$ and $R^8$, a bond between $R^8$ and $R^9$, a bond between $R^1$ and $R^9$, a bond between $R^{a1}$ and $R^{a2}$, and a bond between substituents which may be included in A. However, in a case where $R^6$ and $R^7$, $R^7$ and $R^8$, and $R^8$ and $R^9$ bond to each other to form a ring, the ring does not include an aromatic ring.

A compound represented by Formula (2) does not contain both an acidic group and a salt thereof.

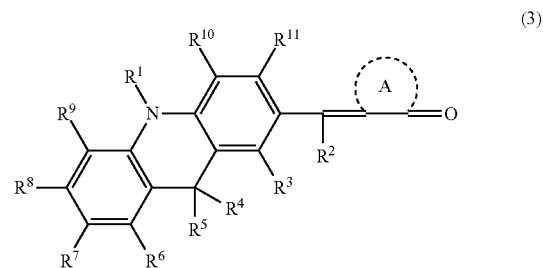

(3)

In Formula (3), $R^1$ to $R^9$, and A are the same as $R^1$ to $R^9$, and A in Formula (2), respectively, and the preferred embodiments are also the same.

$R^{10}$ and $R^{11}$ each independently represent a hydrogen atom or a substituent. Examples of the substituent represented by $R^{10}$ and $R^{11}$ include those similar to $R^{a1}$ and $R^{a2}$ described above.

$R^6$ to $R^9$ are each preferably a hydrogen atom or an aryl group which may have a substituent, from the viewpoint of smaller dependency on the substrate temperature during vapor deposition.

In Formula (3), the respective substituents may bond to each other to form a ring. The respective substituents used herein refer to each of the substituents represented by $R^1$ to $R^{11}$ and the substituents which may be included in A. Specific embodiments in which the respective substituents bond to each other include a bond between $R^2$ and $R^3$, a bond between $R^3$ and $R^4$, a bond between $R^4$ and $R^5$, a bond between $R^5$ and $R^6$, a bond between $R^6$ and $R^7$, a bond between $R^7$ and $R^8$, a bond between $R^8$ and $R^9$, a bond between $R^{10}$ and $R^{11}$, a bond between $R^1$ and $R^9$, a bond between $R^1$ and $R^{10}$, and a bond between substituents which may be included in A. However, in a case where $R^6$ and $R^7$, $R^7$ and $R^8$, and $R^8$ and $R^9$ bond to each other to form a ring, the ring does not include an aromatic ring.

A compound represented by Formula (3) does not contain both an acidic group and a salt thereof.

From the viewpoint of smaller dependency on the substrate temperature during vapor deposition and smaller dependency of the photoelectric conversion efficiency on the composition ratio, the compound represented by Formula (3) is still more preferably a compound represented by Formula (4).

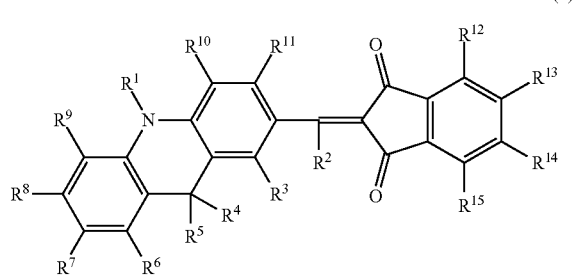

(4)

In Formula (4), $R^1$ to $R^{11}$ are the same as $R^1$ to $R^{11}$ in Formula (3), respectively, and the preferred embodiments are also the same.

$R^{12}$ to $R^{15}$ each independently represent a hydrogen atom or a substituent. Examples of the substituent represented by $R^{12}$ to $R^{15}$ include the same substituents that may be included in A.

$R^6$ to $R^9$ are each preferably a hydrogen atom or an aryl group which may have a substituent, from the viewpoint of smaller dependency on the substrate temperature during vapor deposition.

In Formula (4), the respective substituents may bond to each other to form a ring. The respective substituent used herein refer to each of the substituents represented by $R^1$ to $R^{15}$. Specific embodiments in which the respective substituents bond to each other include a bond between $R^2$ and $R^3$, a bond between $R^3$ and $R^4$, a bond between $R^4$ and $R^5$, a bond between $R^5$ and $R^6$, a bond between $R^6$ and $R^7$, a bond between $R^7$ and $R^8$, a bond between $R^8$ and $R^9$, a bond between $R^{10}$ and $R^{11}$, a bond between $R^1$ and $R^9$, a bond between $R^1$ and $R^{10}$, a bond between $R^{12}$ and $R^{13}$, a bond between $R^{13}$ and $R^{14}$, and a bond between $R^{14}$ and $R^{15}$. However, in a case where $R^6$ and $R^7$, $R^7$ and $R^8$, and $R^8$ and $R^9$ bond to each other to form a ring, the ring does not include an aromatic ring.

In a case where $R^{12}$ and $R^{13}$, $R^{13}$ and $R^{14}$, and $R^{14}$ and $R^{15}$ bond to each other to form a ring, the type of the ring is not limited, but may be an aromatic ring or an aliphatic ring, and is preferably a benzene ring.

A compound represented by Formula (4) does not contain both an acidic group and a salt thereof.

Substituent W

The substituent W in the present specification will be described below.

Examples of the substituent W include a halogen atom (a fluorine atom, a chlorine atom, a bromine atom, an iodine atom, and the like), an alkyl group (including a cycloalkyl group, a bicycloalkyl group, and a tricycloalkyl group), an alkenyl group (including a cycloalkenyl group and a bicycloalkenyl group), an alkynyl group, an aryl group, a heterocyclic group (including a heteroaryl group), a cyano group, a hydroxy group, a nitro group, an alkoxy group, an aryloxy group, a silyloxy group, a heterocyclic oxy group, an acyloxy group, a carbamoyloxy group, an alkoxycarbonyloxy group, an aryloxycarbonyloxy group, an amino group (including an anilino group), an ammonium group, an acylamino group, an aminocarbonylamino group, an alkoxycarbonylamino group, an aryloxycarbonylamino group, a sulfamoylamino group, an alkyl- or arylsulfonylamino group, an alkylthio group, an arylthio group, a heterocyclic thio group, a sulfamoyl group, an alkyl- or arylsulfinyl group, an alkyl- or arylsulfonyl group, an acyl group, an aryloxycarbonyl group, an alkoxycarbonyl group, a carbamoyl group, an aryl- or heterocyclic azo group, an imide group, a phosphino group, a phosphinyl group, a phosphinyloxy group, a phosphinylamino group, a phosphono group, a silyl group, a hydrazino group, a ureido group, and other well-known substituents.

Also, the substituent W may be further substituted with the substituent W. For example, an alkyl group may be substituted with a halogen atom.

The details of the substituent W are disclosed in paragraph [0023] of JP2007-234651A.

Although the specific compound is exemplified below, the specific compound in the invention is not limited thereto.

In the following examples, in a case where the exemplified compound is applied to Formula (1), the exemplified compound includes both the cis isomer and the trans isomer for the geometric isomer which is distinguished based on a group corresponding to the C=C double bond constituted by a carbon atom to which $R^2$ bonds and a carbon atom adjacent thereto.

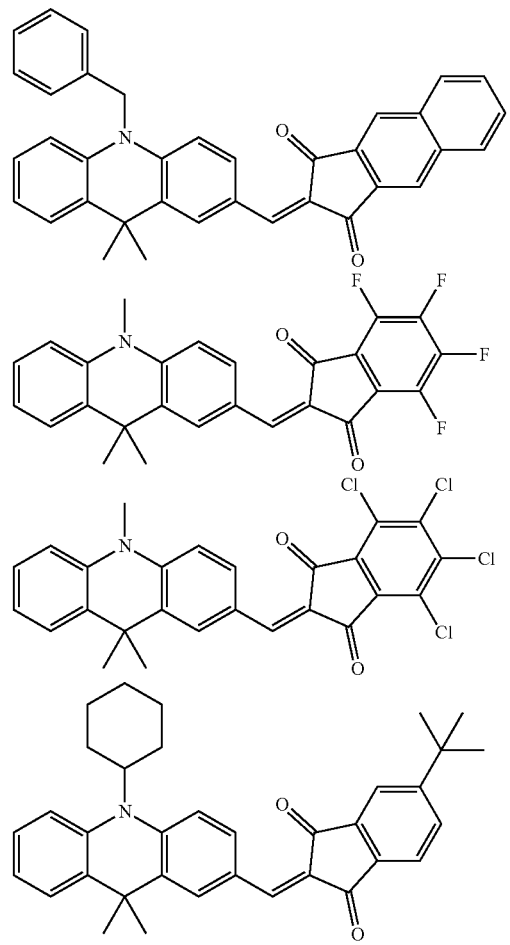

15
-continued
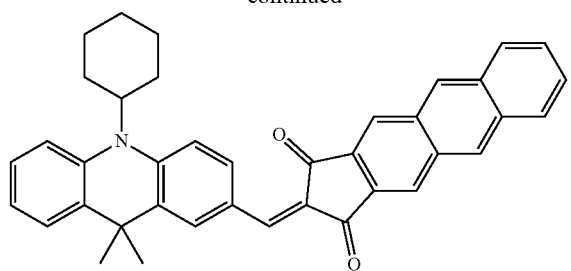
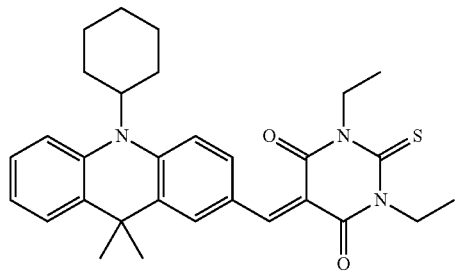
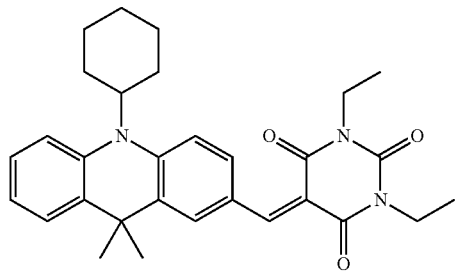
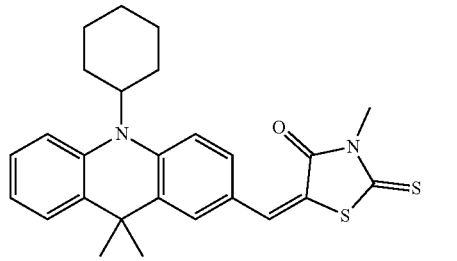
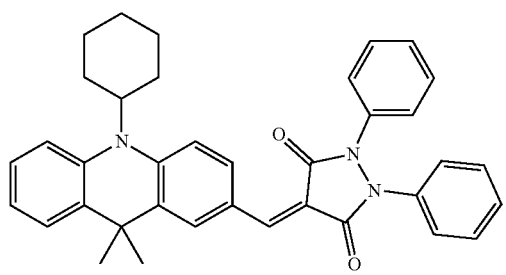
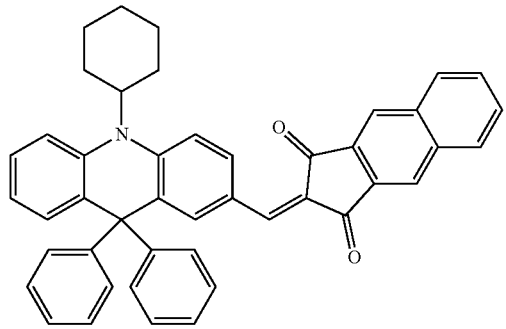
16
-continued
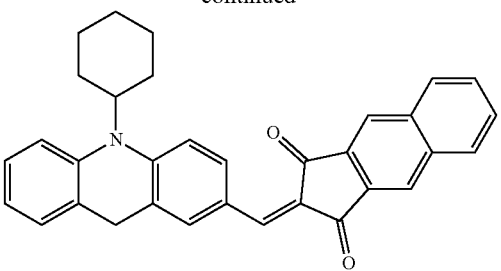
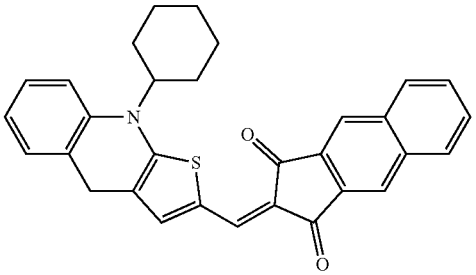
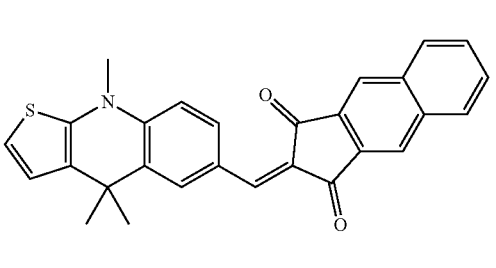
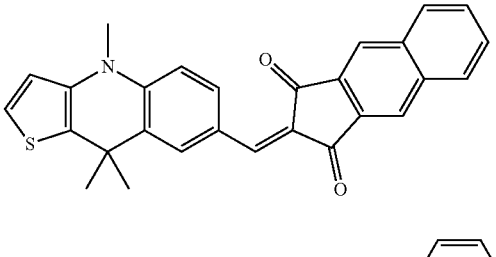
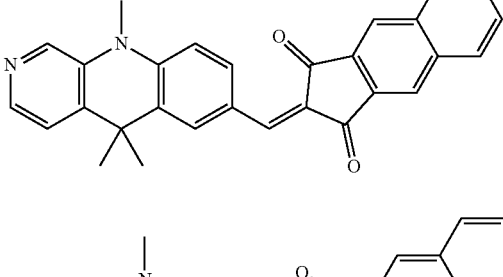
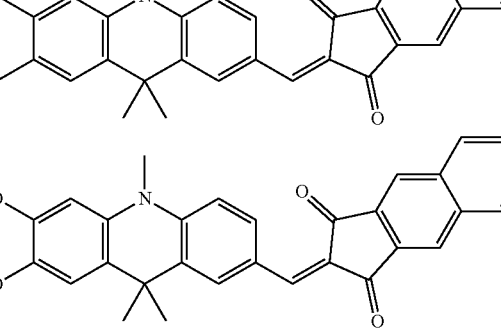

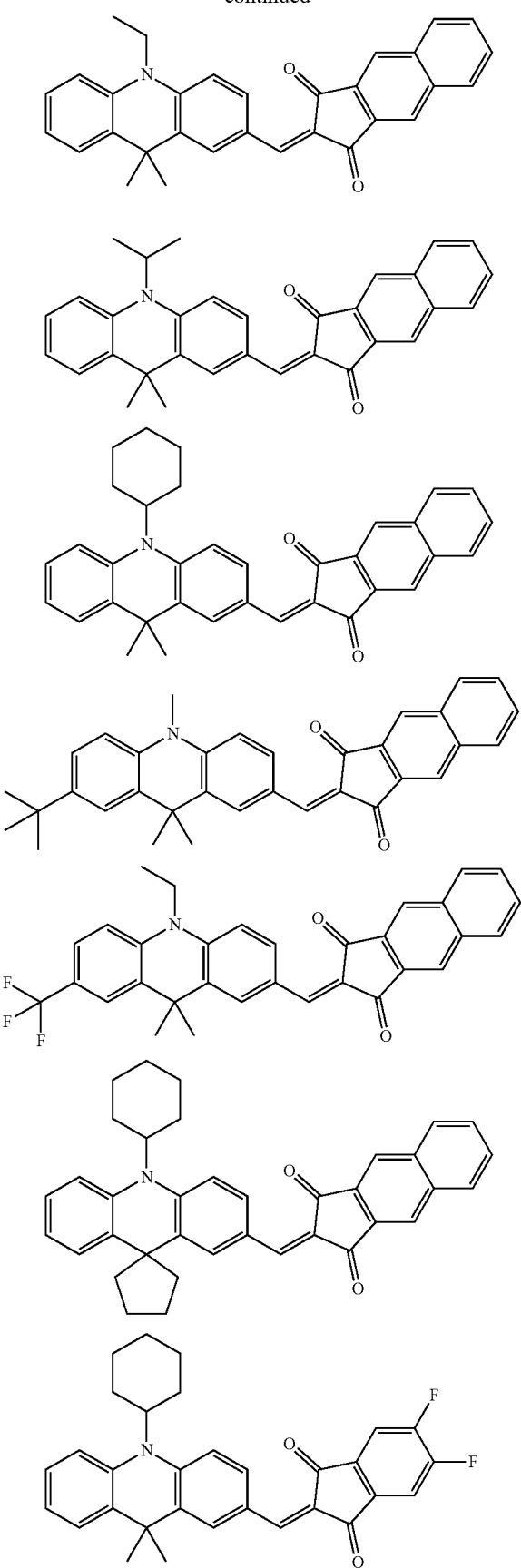

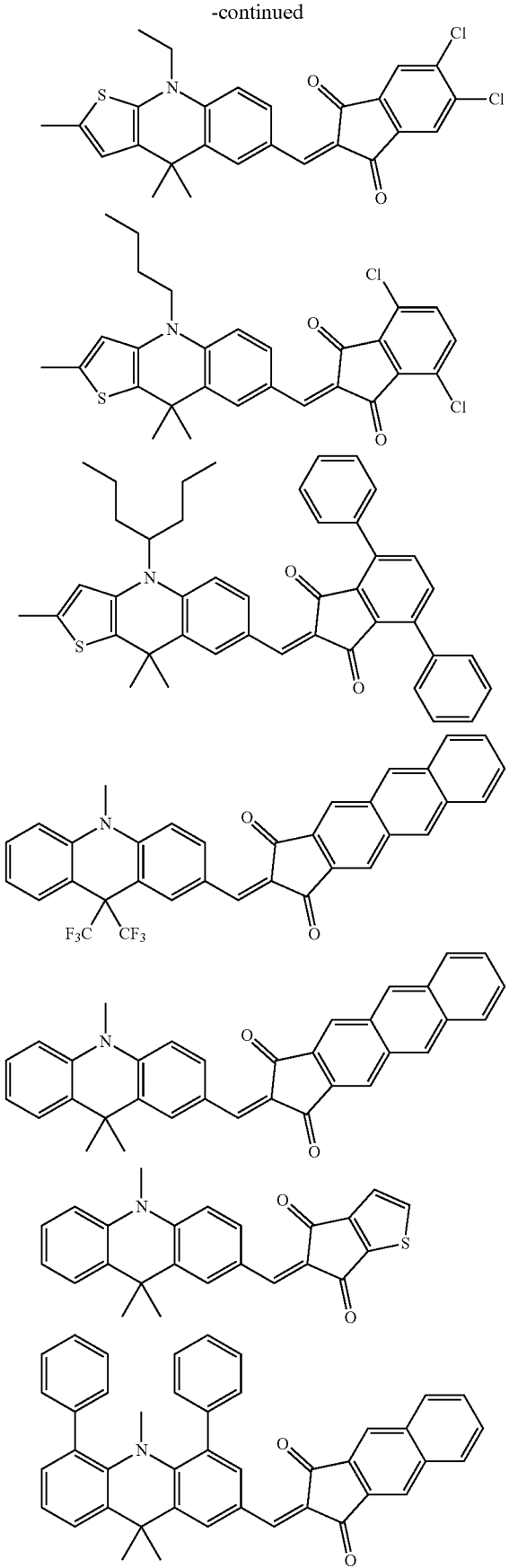
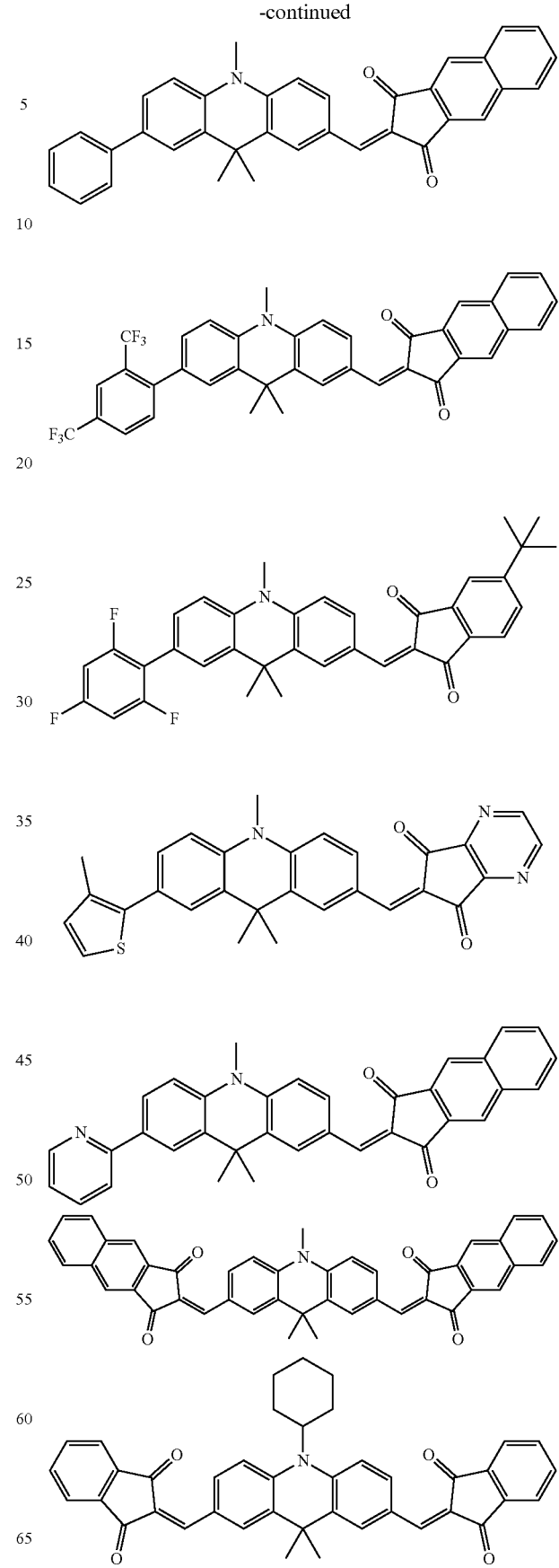

-continued

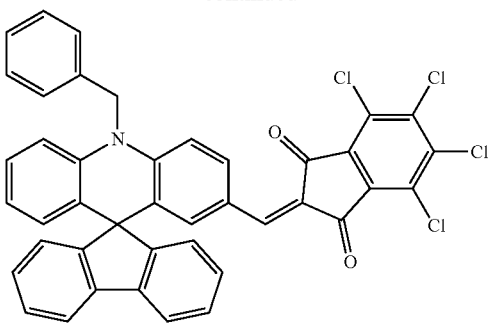

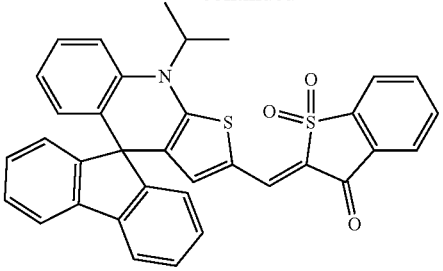

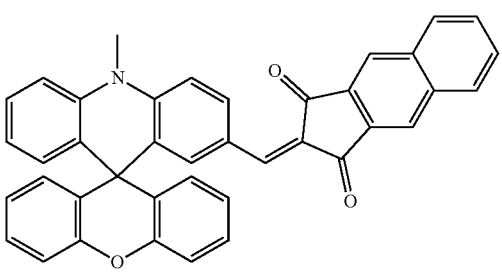

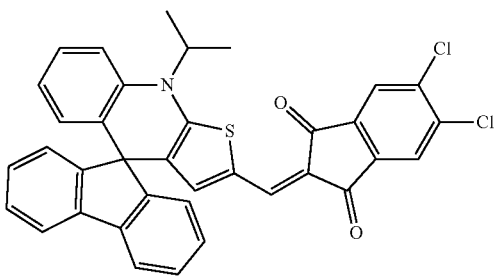

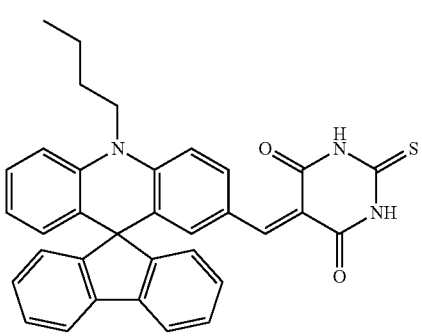

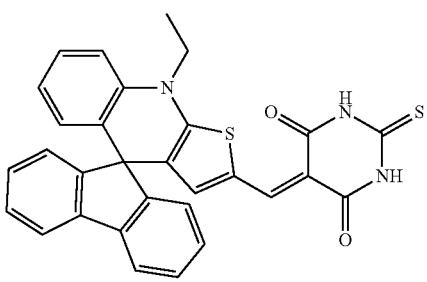

A molecular weight of the specific compound is not particularly limited, but is preferably 400 to 1000. In a case where the molecular weight is 400 or more, a glass transition point of a deposited film does not decrease, and a heat resistance of the photoelectric conversion element is further improved. In a case where the molecular weight is 1000 or less, the vapor deposition temperature does not increase, and the decomposition of the compound hardly occurs.

The specific compound is particularly useful as a material of the photoelectric conversion film used for the optical sensor, the imaging element, or a photoelectric cell. In addition, the specific compound usually functions as the p-type organic semiconductor in the photoelectric conversion film in many cases. The specific compound can also be used as a coloring material, a liquid crystal material, an organic semiconductor material, a charge transport material, a pharmaceutical material, and a fluorescent diagnostic material.

The specific compound is preferably a compound in which an ionization potential in a single film is −5.0 to −6.0 eV from the viewpoints of stability in a case of using the compound as the p-type organic semiconductor and matching of energy levels between the compound and the n-type organic semiconductor.

In order to be applicable to the organic photoelectric conversion film 209 that absorbs green light and performs photoelectric conversion, the maximum absorption wavelength of the specific compound is preferably in the range of 420 to 650 nm, and is more preferably in the range of 480 to 600 nm.

The maximum absorption wavelength is a value measured in a solution state (solvent: chloroform) by adjusting the absorption spectrum of the specific compound to a concentration such that the light absorbance is 0.5 to 1.

n-Type Organic Semiconductor

It is preferable that the photoelectric conversion film contains the n-type organic semiconductor as a component other than the specific compound.

The n-type organic semiconductor is an acceptor-property organic semiconductor material (a compound), and refers to an organic compound having a property of easily accepting an electron. More specifically, the n-type organic semiconductor refers to an organic compound having a large electron affinity of two organic compounds used in contact with each other.

Examples of the n-type organic semiconductor include a condensed aromatic carbocyclic compound (for example, fullerene, a naphthalene derivative, an anthracene derivative, a phenanthrene derivative, a tetracene derivative, a pyrene derivative, a perylene derivative, and a fluoranthene derivative); a 5 to 7 membered heterocyclic compound having at least one of a nitrogen atom, an oxygen atom, or a sulfur atom (for example, pyridine, pyrazine, pyrimidine, pyridazine, triazine, quinoline, quinoxaline, quinazoline, phthalazine, cinnoline, isoquinoline, pteridine, acridine, phenazine, phenanthroline, tetrazole, pyrazole, imidazole, and thiazole); a polyarylene compound; a fluorene compound; a cyclopentadiene compound; a silyl compound; and a metal complex having a nitrogen-containing heterocyclic compound as the ligands.

An organic dye may be used as the n-type organic semiconductor. Examples of the organic dye include a cyanine dye, a styryl dye, a hemicyanine dye, a merocyanine dye (including zeromethine merocyanine (simple merocyanine)), a rhodacyanine dye, an allopolar dye, an oxonol dye, a hemioxonol dye, a squarylium dye, a croconium dye, an azamethine dye, a coumarin dye, an arylidene dye, an anthraquinone dye, a triphenylmethane dye, an azo dye, an azomethine dye, a metallocene dye, a fluorenone dye, a flugide dye, a perylene dye, a phenazine dye, a phenothiazine dye, a quinone dye, a diphenylmethane dye, a polyene dye, an acridine dye, an acridinone dye, a diphenylamine dye, a quinophthalone dye, a phenoxazine dye, a phthaloperylene dye, a dioxane dye, a porphyrin dye, a chlorophyll dye, a phthalocyanine dye, a subphthalocyanine dye, and a metal complex dye.

The molecular weight of the n-type organic semiconductor is preferably 200 to 1200, and more preferably 400 to 1000.

On the other hand, in a case of the form as shown in FIG. 2, it is desirable that the n-type organic semiconductor is colorless, or has the maximum absorption wavelength and/or an absorption waveform close to that of the specific compound, and a specific value of the maximum absorption wavelength of the n-type organic semiconductor is desirably 400 nm or less, or 500 to 600 nm.

It is preferable that the photoelectric conversion film has a bulk hetero structure formed in a state in which the specific compound and the n-type organic semiconductor are mixed. The bulk hetero structure refers to a layer in which the specific compound and the n-type organic semiconductor are mixed and dispersed in the photoelectric conversion film. The photoelectric conversion film having the bulk hetero structure can be formed by either a wet method or a dry method. The bulk hetero structure is described in detail in, for example, paragraphs [0013] to [0014] of JP2005-303266A.

The content of the specific compound to the total content of the specific compound and the n-type organic semiconductor (=film thickness in terms of single layer of specific compound/(film thickness in terms of single layer of specific compound+film thickness in terms of single layer of n-type organic semiconductor)×100) is preferably 20 to 80 volume %, more preferably 30 to 70 volume %, and still more preferably 40 to 60 volume % from the viewpoint of responsiveness of the photoelectric conversion element.

It is preferable that the photoelectric conversion film is substantially formed of the specific compound and the n-type organic semiconductor. The term "substantially" means that the total content of the specific compound and the n-type organic semiconductor to the total mass of the photoelectric conversion film is 95 mass % or more.

The n-type organic semiconductor contained in the photoelectric conversion film may be used alone, or by a combination of two or more types.

The photoelectric conversion film may further contain a p-type organic semiconductor in addition to the specific compound and the n-type organic semiconductor. Examples of the p-type organic semiconductor include examples shown below.

In a case where the specific compound is used as the p-type organic semiconductor, the p-type organic semiconductor intends the p-type organic semiconductor other than the specific compound.

p-Type Organic Semiconductor

The p-type organic semiconductor is a donor-property organic semiconductor material (a compound), and refers to an organic compound having a property of easily donating an electron. More specifically, the p-type organic semiconductor refers to an organic compound having an ionization potential of two organic compounds used in contact with each other.

Examples of the p-type organic semiconductor (the p-type organic semiconductor other than the specific compound) include a triarylamine compound, a benzidine compound, a pyrazoline compound, a styrylamine compound, a hydrazone compound, a carbazole compound, a polysilane compound, a thiophene compound, a cyanine compound, an oxonol compound, a polyamine compound, an indole compound, a pyrrole compound, a pyrazole compound, a polyarylene compound, a condensed aromatic carbocyclic compound, and metal complexes having a nitrogen-containing heterocyclic compound as ligands.

Examples of the p-type organic semiconductor include a compound having an ionization potential smaller than that of the n-type organic semiconductor. When this condition is satisfied, the organic dye exemplified as the n-type organic semiconductor can be used.

The photoelectric conversion film containing the specific compound is a non-luminescent film, and has a feature different from an organic light emitting diode (OLED). The non-luminescent film means a film having a luminescence quantum efficiency of 1% or less, and the luminescence quantum efficiency is preferably 0.5% or less, and more preferably 0.1% or less.

Film Formation Method

The photoelectric conversion film can be formed mostly by a dry film formation method. Specific examples of the dry film formation method include a physical vapor deposition method such as a vapor deposition method (in particular, a vacuum evaporation method), a sputtering method, an ion plating method, and molecular beam epitaxy (MBE), and chemical vapor deposition (CVD) such as plasma polymerization. Among these, the vacuum evaporation method is preferable. In a case where the photoelectric conversion film is formed by the vacuum evaporation method, a producing condition such as a degree of vacuum and a vapor deposition temperature can be set according to the normal method.

The thickness of the photoelectric conversion film is preferably 10 to 1000 nm, more preferably 50 to 800 nm, still more preferably 50 to 500 nm, and particularly preferably 50 to 300 nm.

Electrode

The electrode (the upper electrode (the transparent conductive film) 15 and the lower electrode (the conductive film) 11) is formed of a conductive material. Examples of the conductive material include metals, alloys, metal oxides, electrically conductive compounds, and mixtures thereof.

Since light is incident through the upper electrode 15, the upper electrode 15 is preferably transparent to light to be detected. Examples of the material forming the upper electrode 15 include conductive metal oxides such as tin oxide (ATO, FTO) doped with antimony, fluorine, or the like, tin oxide, zinc oxide, indium oxide, indium tin oxide (ITO), and indium zinc oxide (IZO); metal thin films such as gold, silver, chromium, and nickel; mixtures or laminates of these metals and the conductive metal oxides; and organic conductive materials such as polyaniline, polythiophene, and polypyrrole. Among these, conductive metal oxides are preferable from the viewpoints of high conductivity, transparency, and the like.

In general, in a case where the conductive film is made to be thinner than a certain range, a resistance value is rapidly increased. However, in the solid-state imaging element into which the photoelectric conversion element according to the present embodiment is incorporated, the sheet resistance is preferably 100 to 10000Ω/□, and the degree of freedom of the range of the film thickness that can be thinned is large. In addition, as the thickness of the upper electrode (the transparent conductive film) 15 is thinner, the amount of light that the upper electrode absorbs becomes smaller, and the light transmittance usually increases. The increase in the light transmittance causes an increase in light absorbance in the photoelectric conversion film and an increase in the photoelectric conversion ability, which is preferable. Considering the suppression of leakage current, an increase in the resistance value of the thin film, and an increase in transmittance accompanied by the thinning, the film thickness of the upper electrode 15 is preferably 5 to 100 nm, and more preferably 5 to 20 nm.

There is a case where the lower electrode 11 has transparency or an opposite case where the lower electrode does not have transparency and reflects light, depending on the application. Examples of a material constituting the lower electrode 11 include conductive metal oxides such as tin oxide (ATO, FTO) doped with antimony, fluorine, or the like, tin oxide, zinc oxide, indium oxide, indium tin oxide (ITO), and indium zinc oxide (IZO); metals such as gold, silver, chromium, nickel, titanium, tungsten, and aluminum, conductive compounds (for example, titanium nitride (TiN)) such as oxides or nitrides of these metals; mixtures or laminates of these metals and conductive metal oxides; and organic conductive materials such as polyaniline, polythiophene, and polypyrrole.

The method of forming electrodes is not particularly limited, and can be appropriately selected in accordance with the electrode material. Specific examples thereof include a wet method such as a printing method and a coating method; a physical method such as a vacuum evaporation method, a sputtering method, and an ion plating method; and a chemical method such as a CVD method and a plasma CVD method.

In a case where the material of the electrode is ITO, examples thereof include an electron beam method, a sputtering method, a resistance thermal vapor deposition method, a chemical reaction method (such as a sol-gel method), and a coating method with a dispersion of indium tin oxide.

Charge Blocking Film: Electron Blocking Film and Positive Hole Blocking Film

It is also preferable that the photoelectric conversion element of the embodiment of the invention has one or more interlayers between the conductive film and the transparent conductive film, in addition to the photoelectric conversion film. Example of the interlayer includes the charge blocking film. In the case where the photoelectric conversion element has this film, the characteristics (such as photoelectric conversion efficiency and responsiveness) of the photoelectric conversion element to be obtained become superior. Examples of the charge blocking film include the electron blocking film and the positive hole blocking film. Hereinafter, the films will be described in detail.

Electron Blocking Film

The electron blocking film includes an electron donating compound. Specific examples of a low molecular material include aromatic diamine compounds such as N,N'-bis(3-methylphenyl)-(1,1'-biphenyl)-4,4'-diamine (TPD) and 4,4'-bis[N-(naphthyl)-N-phenyl-amino] biphenyl (α-NPD); porphyrin compounds such as porphyrin, copper tetraphenylporphyrin, phthalocyanine, copper phthalocyanine, and titanium phthalocyanine oxide; and oxazole, oxadiazole, triazole, imidazole, imidazolone, a stilbene derivative, a pyrazoline derivative, tetrahydroimidazole, polyarylalkane, butadiene, 4,4',4"-tris(N-(3-methylphenyl)-N-phenylamino) triphenylamine (m-MTDATA), a triazole derivative, an oxadiazole derivative, an imidazole derivative, a polyarylalkane derivative, a pyrazoline derivative, a pyrazolone derivative, a phenylenediamine derivative, an arylamine derivative, an amino-substituted chalcone derivative, an oxazole derivative, a styrylanthracene derivative, a fluorenone derivative, a hydrazone derivative, and a silazane derivative. Specific examples of a polymer material include a polymer such as phenylenevinylene, fluorene, carbazole, indole, pyrene, pyrrole, picoline, thiophene, acetylene, and diacetylene, and a derivative thereof. In addition, compounds described in paragraphs [0049] to [0063] of JP5597450B, compounds described in paragraphs [0119] to [0158] of JP2011-225544A, and compounds described in paragraphs [0086] to [0090] of JP2012-094660A are exemplified.

The electron blocking film may be configured by a plurality of films.

The electron blocking film may be formed of an inorganic material. In general, an inorganic material has a dielectric constant larger than that of an organic material. Therefore, in a case where the inorganic material is used in the electron blocking film, a large voltage is applied to the photoelectric conversion film. Therefore, the photoelectric conversion efficiency increases. Examples of the inorganic material that can be used in the electron blocking film include calcium oxide, chromium oxide, copper chromium oxide, manganese oxide, cobalt oxide, nickel oxide, copper oxide, copper gallium oxide, copper strontium oxide, niobium oxide, molybdenum oxide, copper indium oxide, silver indium oxide, and iridium oxide.

Positive Hole Blocking Film

The positive hole blocking film includes an electron accepting compound.

Examples of the electron accepting compound include an oxadiazole derivative such as 1,3-bis(4-tert-butylphenyl-1,3,4-oxadiazolyl)phenylene (OXD-7); an anthraquinodimethane derivative; a diphenylquinone derivative; bathocuproine, bathophenanthroline, and derivatives thereof; a triazole compound; a tris(8-hydroxyquinolinato)aluminum complex; a bis(4-methyl-8-quinolinato)aluminum complex; a distyrylarylene derivative; and a silole compound. In addition, compounds described in paragraphs [0056] to [0057] of JP2006-100767A are exemplified.

The method of producing the charge blocking film is not particularly limited, a dry film formation method and a wet film formation method are exemplified. Examples of the dry film formation method include a vapor deposition method and a sputtering method. The vapor deposition method may be any of physical vapor deposition (PVD) method and chemical vapor deposition (CVD) method, and physical vapor deposition method such as vacuum evaporation method is preferable. Examples of the wet film formation method include an inkjet method, a spray method, a nozzle printing method, a spin coating method, a dip coating method, a casting method, a die coating method, a roll coating method, a bar coating method, and a gravure coating method, and an inkjet method is preferable from the viewpoint of high precision patterning.

Each thickness of the charge blocking films (the electron blocking film and the positive hole blocking film) is preferably 3 to 200 nm, more preferably 5 to 100 nm, and still more preferably 5 to 30 nm.

Substrate

The photoelectric conversion element may further include a substrate. The type of substrate to be used is not particularly limited, and a semiconductor substrate, a glass substrate, and a plastic substrate are exemplified.

The position of the substrate is not particularly limited, but in general, the conductive film, the photoelectric conversion film, and the transparent conductive film are laminated on the substrate in this order.

Sealing Layer

The photoelectric conversion element may further include a sealing layer. The performance of the photoelectric conversion material may deteriorate noticeably due to the presence of deterioration factors such as water molecules. The deterioration can be prevented by sealing and coating the entirety of the photoelectric conversion film with the sealing layer such as diamond-like carbon (DLC) or ceramics such as metal oxide, or metal nitride, and metal nitride oxide which are dense and into which water molecules do not permeate.

The material of the sealing layer may be selected and the sealing layer may be produced according to the description in paragraphs [0210] to [0215] of JP2011-082508A.

Optical Sensor

Examples of the application of the photoelectric conversion element include the photoelectric cell and the optical sensor, but the photoelectric conversion element of the embodiment of the invention is preferably used as the optical sensor. The photoelectric conversion element may be used alone as the optical sensor. Alternately, the photoelectric conversion element may be used as a line sensor in which the photoelectric conversion elements are linearly arranged or as a two-dimensional sensor in which the photoelectric conversion elements are planarly arranged. In the line sensor of the embodiment of the invention, the photoelectric conversion element of the invention functions as the imaging element by converting optical image information into an electric signal using an optical system such as a scanner, and a driving unit. In the two-dimensional sensor, the photoelectric conversion element of the invention functions as the imaging element by converting the optical image information into the electric signal by imaging the optical image information on the sensor using the optical system such as an imaging module.

Imaging Element

Next, a configuration example of an imaging element comprising the photoelectric conversion element 10a will be described.

In the configuration example which will be described below, the same reference numerals or the corresponding reference numerals are attached to members or the like having the same configuration or action as those which have already been described, to simplify or omit the description.

The imaging element is an element that converts optical information of an image into the electric signal, and is an element in which a plurality of photoelectric conversion elements are arranged on a matrix in the same planar form, optical signals are converted into electric signals in each photoelectric conversion element (a pixel), and the electric signals can be sequentially output to the outside of the imaging elements for each pixel. For this reason, one pixel is formed of one photoelectric conversion element and one or more transistors.

Figure 3:
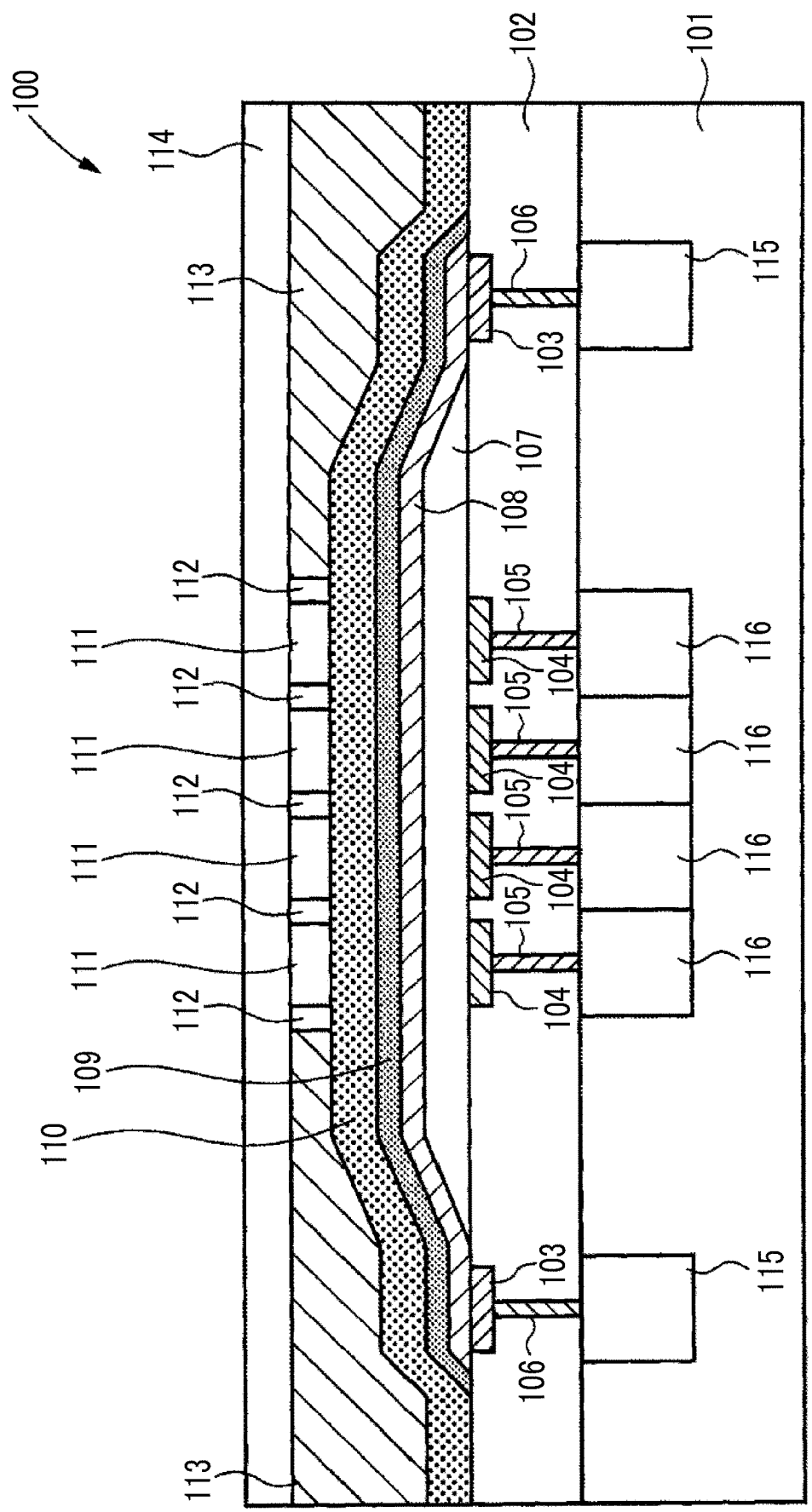
FIG. 3 is a schematic cross-sectional view of one pixel of an imaging element.

FIG. 3 is a schematic cross-sectional view showing a schematic configuration of an imaging element for describing an embodiment of the invention. This imaging element is mounted on an imaging device such as a digital camera and a digital video camera, an electronic endoscope, and imaging modules such as a cellular phone.

The imaging element has a plurality of photoelectric conversion elements having configurations shown in FIG. 1A and a circuit substrate in which the readout circuit reading out signals corresponding to charges generated in the photoelectric conversion film of each photoelectric conversion element is formed. The imaging element has a configuration in which the plurality of photoelectric conversion elements are one-dimensionally or two-dimensionally arranged on the same surface above the circuit substrate.

An imaging element 100 shown in FIG. 3 comprises a substrate 101, an insulating layer 102, connection electrodes 103, pixel electrodes (lower electrodes) 104, connection units 105, connection units 106, a photoelectric conversion film 107, a counter electrode (upper electrode) 108, a buffer layer 109, a sealing layer 110, a color filter (CF) 111, partition walls 112, a light shielding layer 113, a protective layer 114, a counter electrode voltage supply unit 115, and readout circuits 116.

The pixel electrode 104 has the same function as the lower electrode 11 of the photoelectric conversion element 10a shown in FIG. 1A. The counter electrode 108 has the same function as the upper electrode 15 of the photoelectric conversion element 10a shown in FIG. 1A. The photoelectric conversion film 107 has the same configuration as a layer provided between the lower electrode 11 and the upper electrode 15 of the photoelectric conversion element 10a shown in FIG. 1A.

The substrate 101 is a semiconductor substrate such as the glass substrate, or Si. The insulating layer 102 is formed on the substrate 101. A plurality of pixel electrodes 104 and a plurality of connection electrodes 103 are formed on the surface of the insulating layer 102.

The photoelectric conversion film 107 is a layer common to all the photoelectric conversion elements provided so as to cover the plurality of pixel electrodes 104.

The counter electrode 108 is one electrode common to all the photoelectric conversion elements provided on the photoelectric conversion film 107. The counter electrode 108 is formed on the connection electrodes 103 arranged on an outer side than the photoelectric conversion film 107, and is electrically connected to the connection electrodes 103.

The connection units 106 are buried in the insulating layer 102, and are plugs for electrically connecting the connection electrodes 103 to the counter electrode voltage supply unit 115. The counter electrode voltage supply unit 115 is formed in the substrate 101, and applies a predetermined voltage to the counter electrode 108 via the connection units 106 and the connection electrodes 103. In a case where a voltage to be applied to the counter electrode 108 is higher than a power supply voltage of the imaging element, the power supply voltage is boosted by a boosting circuit such as a charge pump to supply the predetermined voltage.

The readout circuits 116 are provided on the substrate 101 corresponding to each of the plurality of pixel electrodes 104, and read out signals corresponding to charges trapped by the corresponding pixel electrodes 104. The readout circuits 116 are configured, for example, of CCD and CMOS circuits, or a thin film transistor (TFT) circuit, and are shielded by the light shielding layer not shown in the drawing which is disposed in the insulating layer 102. The readout circuits 116 are electrically connected to the corresponding the pixel electrodes 104 via the connection units 105.

The buffer layer 109 is formed on the counter electrode 108 so as to cover the counter electrode 108. The sealing layer 110 is formed on the buffer layer 109 so as to cover the buffer layer 109. The color filters 111 are formed on the sealing layer 110 at positions corresponding to each of the pixel electrodes 104. The partition walls 112 are provided between the color filters 111, and are used for improving the light transmittance of the color filters 111.

The light shielding layer 113 is formed on the sealing layer 110 in a region other than the region where the color filters 111 and the partition walls 112 are provided, and prevents light from being incident to the photoelectric conversion film 107 formed outside an effective pixel region. The protective layer 114 is formed on the color filters 111, the partition walls 112, and the light shielding layer 113, and protects the entirety of the imaging element 100.

In the imaging element 100 configured as described above, light which has entered is incident on the photoelectric conversion film 107, and charges are generated in the photoelectric conversion film. The positive holes among the generated charges are trapped by the pixel electrodes 104, and voltage signals corresponding to the amount are output to the outside of the imaging element 100 using the readout circuits 116.

A method of producing the imaging element 100 is as follows.

The connection units 105 and 106, the plurality of connection electrodes 103, the plurality of pixel electrodes 104, and the insulating layer 102 are formed on the circuit substrate in which the counter electrode voltage supply unit 115 and the readout circuits 116 are formed. The plurality of pixel electrodes 104 are disposed, for example, on the surface of the insulating layer 102 in a square lattice shape.

Next, the photoelectric conversion film 107 is formed on the plurality of pixel electrodes 104, for example, by the vacuum evaporation method. Next, the counter electrode 108 is formed on the photoelectric conversion film 107 under vacuum, for example, by the sputtering method. Next, the buffer layer 109 and the sealing layer 110 are sequentially formed on the counter electrode 108, for example, by the vacuum evaporation method. Next, after the color filters 111, the partition walls 112, and the light shielding layer 113 are formed, the protective layer 114 is formed, and the production of the imaging element 100 is completed.

EXAMPLES

Hereinafter, the invention will be described in more detail based on examples. The materials, use amounts, ratios, processing details, processing procedures, and the like shown in the following examples can be changed as appropriate without departing from the scope of the invention. Therefore, the scope of the present invention should not be construed as being limited by the following examples.

Synthesis Example of Compound Represented by Formula (1)

Hereinafter, as an example of the synthesis of a compound (D-1), a method of synthesizing the compound represented by Formula (1) is shown.

Synthesis of Compound (D-1)

A compound (D-1) was synthesized according to the following scheme.

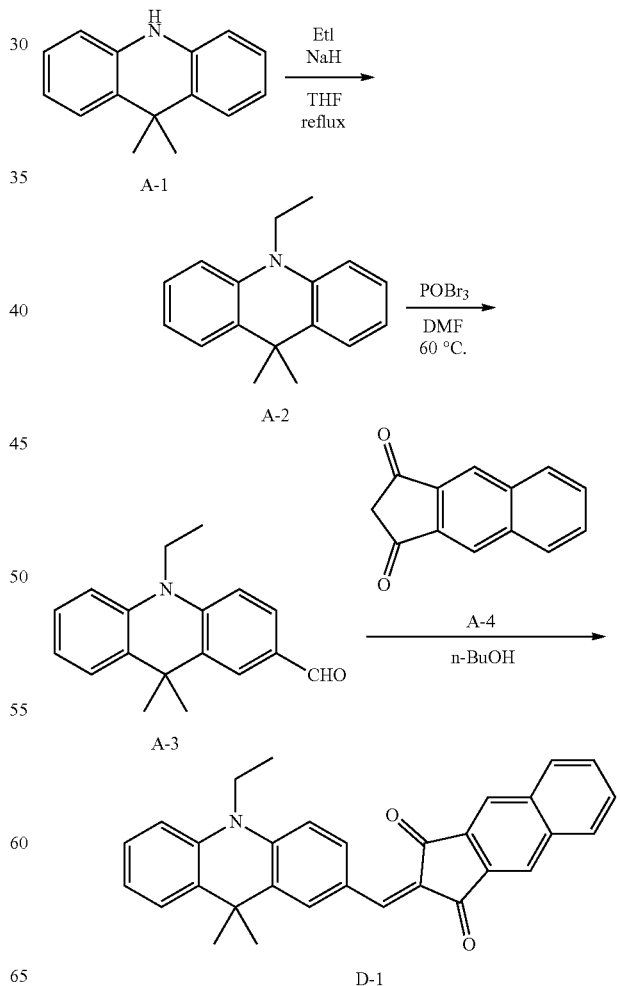

The above compound (A-1) was obtained from Tokyo Chemical Industry and used.

The compound (A-1) (8.00 g, 38.2 mmol), iodoethane (17.9 g, 115 mmol) was dissolved in tetrahydrofuran (115 mL), sodium hydride (60% oil dispersion) (3.66 g, 91.5 mmol) was added thereto, and the mixture was stirred with heating under reflux for 8 hours. After allowing to cool, ice water (1150 mL) was added to the reaction solution, and ethyl acetate was added thereto for extraction. Magnesium sulfate was added to the organic layer and dried, and followed by filtration and concentration to obtain a crude product. The obtained crude product was purified by silica gel column chromatography (eluent: 5% ethyl acetate/hexane) to obtain a compound (A-2) (8.55 g, yield 94%).

The compound (A-2) (8.00 g, 33.7 mmol) was dissolved in N,N'-dimethylformamide (100 mL), and phosphorus oxybromide (9.66 g, 33.7 mmol) was added thereto. The mixture was heated to 60° C. and stirred for 5 hours to be reacted. After cooling to room temperature, the reaction solution was added to a saturated aqueous sodium hydrogen carbonate solution, and extracted with ethyl acetate. Magnesium sulfate was added to the organic layer and dried, and followed by filtration and concentration to obtain a crude product. The obtained crude product was purified by silica gel column chromatography (eluent: 15% ethyl acetate/hexane) to obtain a compound (A-3) (7.66 g, yield 86%).

A compound (A-3) (1.20 g, 4.52 mmol) and a compound (A-4) (0.98 g, 4.97 mmol) were added to n-butanol (24 mL), heated to 90° C., and reacted for 5 hours. After cooling to room temperature, methanol (24 mL) was added to the reaction solution, filtered, and further washed with methanol to obtain a crude product. The obtained crude product was recrystallized from toluene to obtain a compound (D-1) (1.53 g, yield 77%). The compound (A-4) was synthesized according to the procedure disclosed in JP2009-167348A. The obtained compound (D-1) was identified by nuclear magnetic resonance (NMR) and mass spectrometry (MS).

Figure 4:
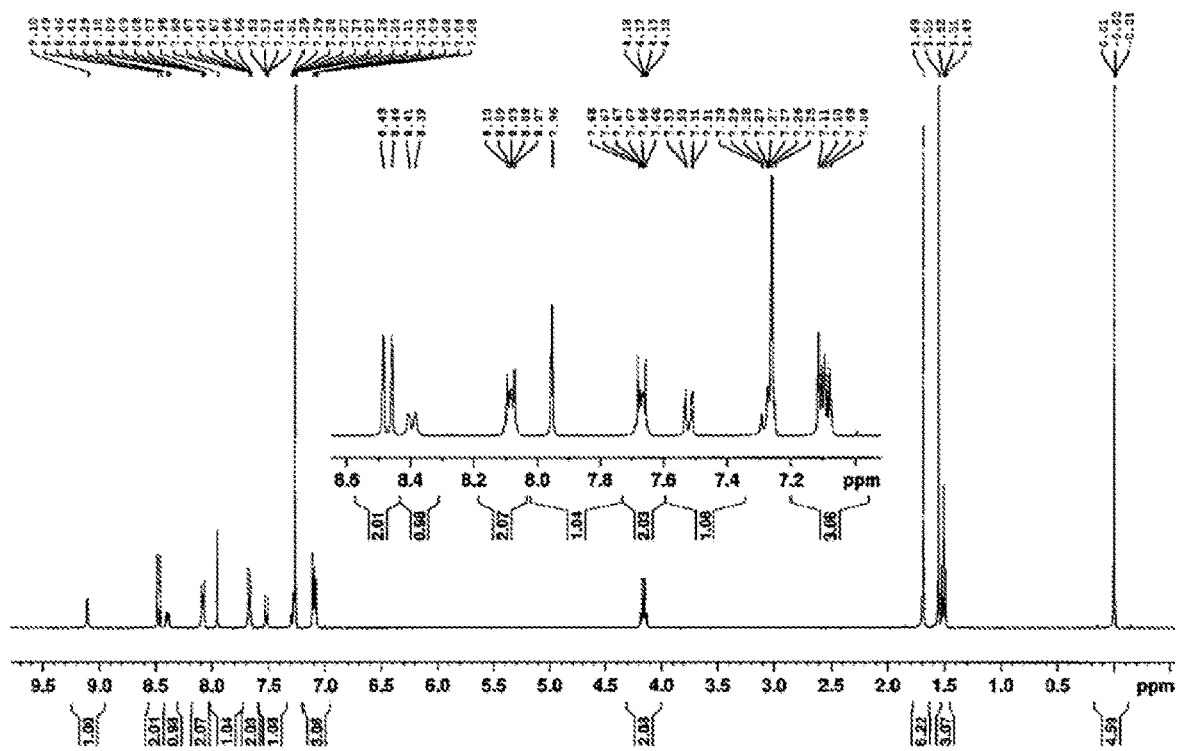
FIG. 4 is a $^1$H NMR spectrum (400 MHz, CDCl$_3$) of a compound D-1.

FIG. 4 shows a $^1$H NMR spectrum (400 MHz, CDCl$_3$).

$^1$MS (ESI$^+$) m/z: 444.1 ([M+H]$^+$)

Figure 5:
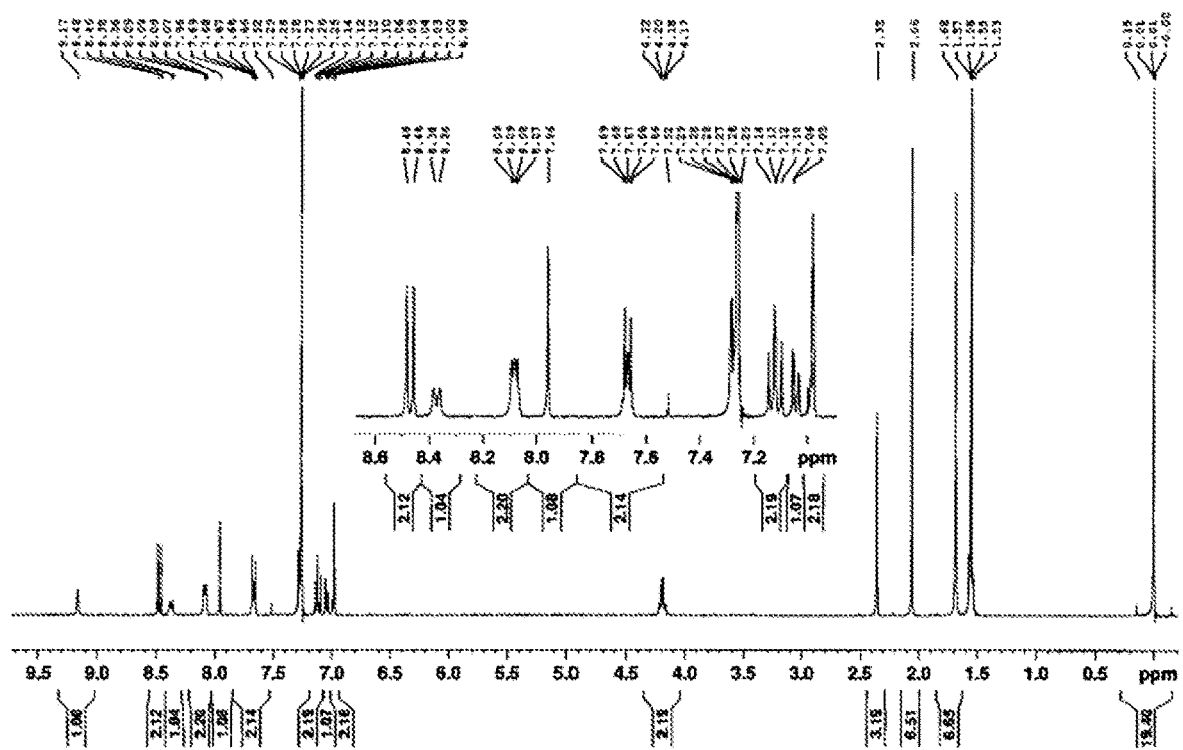
FIG. 5 is a $^1$H NMR spectrum (400 MHz, CDCl$_3$) of a compound D-10.

With reference to the synthesis method of the compound (D-1), compounds (D-2) to (D-12) shown in Example were synthesized. FIG. 5 shows a $^1$H NMR spectrum (400 MHz, CDCl$_3$) of a compound (D-10).

The structures of the compounds (D-1) to (D-12) and the comparative compounds (R-1) to (R-4) are specifically shown below. The comparative compound (R-4) corresponds to an embodiment in which Ar$^1$ is a benzene ring and the substituents on Ar$^1$ bond to each other to form a ring including an aromatic ring.

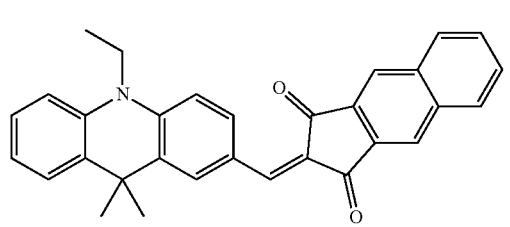

D-1

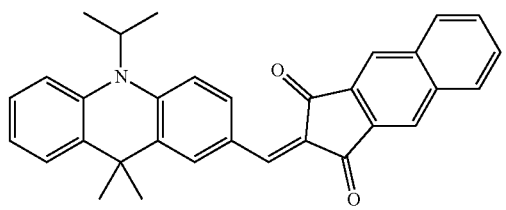

D-2

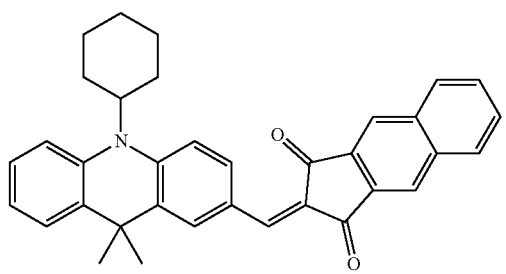

D-3

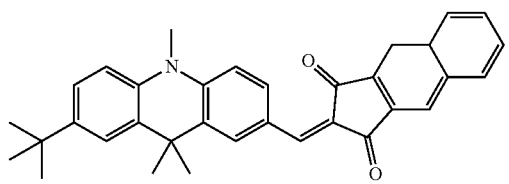

D-4

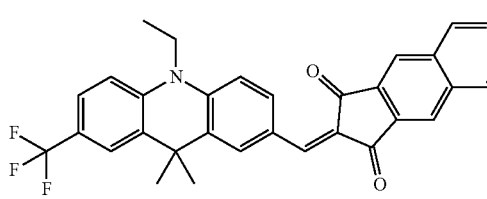

D-5

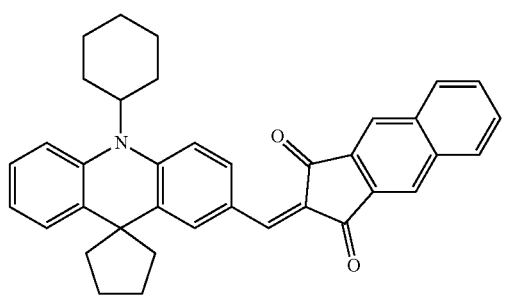

D-6

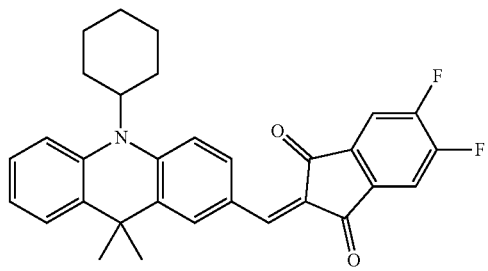

D-7

-continued

D-8
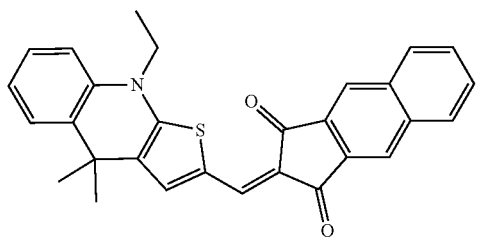

D-9
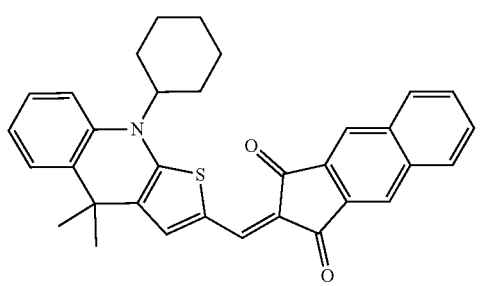

D-10
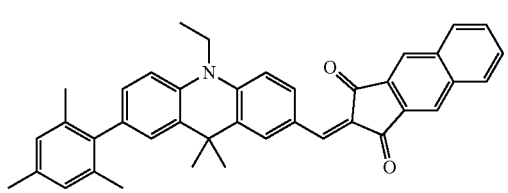

D-11
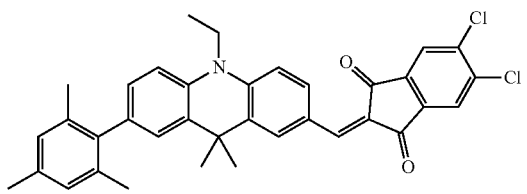

D-12
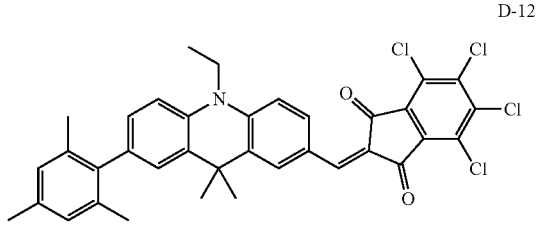

R-1
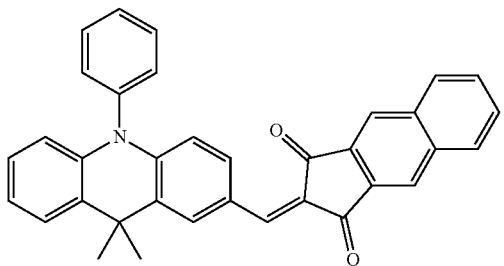

-continued

R-2
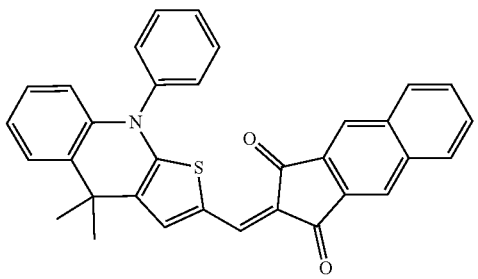

R-3
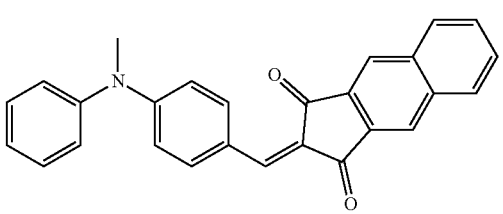

R-4
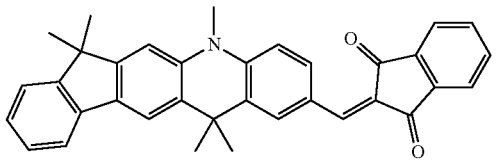

Example 1

Production of Photoelectric Conversion Element

The photoelectric conversion element of the form of FIG. 1A was produced using the obtained compound. Here, the photoelectric conversion element includes the lower electrode 11, the electron blocking film 16A, the photoelectric conversion film 12, and the upper electrode 15. Specifically, an amorphous ITO was formed into a film on the glass substrate by the sputtering method to form the lower electrode 11 (a thickness: 30 nm). Furthermore, the compound (EB-1) was formed into a film on the lower electrode 11 by the vacuum heat evaporation method to form the electron blocking film 16A (a thickness: 30 nm).

Further, with the substrate temperature controlled at 25° C., the compound (D-1) and fullerene (C60) were subjected to co-vapor deposition by the vacuum evaporation method so as to be respectively 100 nm in terms of a single layer on the electron blocking film 16A to form a film, and the photoelectric conversion film 12 of 200 nm was formed.

Furthermore, amorphous ITO was formed into a film on the photoelectric conversion film 12 by a sputtering method to form the upper electrode 15 (the transparent conductive film) (the thickness: 10 nm). After the SiO film was formed as the sealing layer on the upper electrode 15 by a heat evaporation, an aluminum oxide (Al$_2$O$_3$) layer was formed thereon by an atomic layer chemical vapor deposition (AL-CVD) method to produce a photoelectric conversion element.

Note that the photoelectric conversion element produced here, that is, the photoelectric conversion element containing the photoelectric conversion film 12 having the compound (D-1) and fullerene (C60) of respectively 100 nm in terms of a single layer refers to the photoelectric conversion element A1.

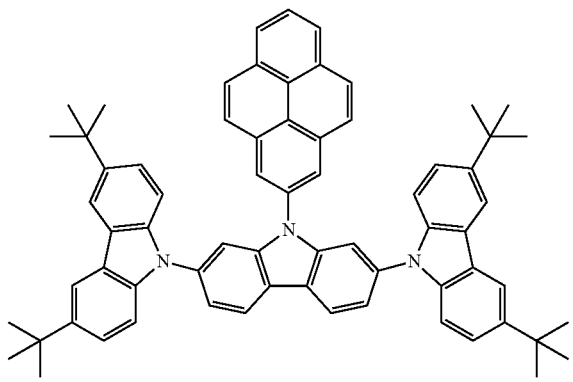

EB-1

Evaluation

Confirmation of Driving

Evaluation of the following operation confirmation was implemented using the obtained photoelectric conversion element A1.

Specifically, a voltage was applied to the photoelectric conversion element A1 so that the electric field strength was $1.0\times10^5$ V/cm. Then, the external quantum efficiency (efficiency in which incident photons were converted into output electrons, hereinafter also referred to as "photoelectric conversion efficiency") in 540 nm was measured by irradiating light from the upper electrode (the transparent conductive film) side.

As a result, it was confirmed that the photoelectric conversion element A1 exhibits the photoelectric conversion efficiency of 60% or more and has sufficient efficiency as a photoelectric conversion element.

The external quantum efficiency was measured using a constant energy quantum efficiency measuring device manufactured by Optel. The amount of light irradiated was 50 µW/cm².

In addition, in the column "driving confirmation" in Table 1, a case where it was confirmed that the photoelectric conversion efficiency is 60% or more and the photoelectric conversion element has sufficient efficiency is indicated as "A".

Evaluation of Dependency on Substrate Temperature During Vapor Deposition

The effect of the substrate temperature on the efficiency during vapor deposition was evaluated.

In the production of the photoelectric conversion element A1 described above, a photoelectric conversion element B1 was produced by the same production method except that the substrate temperature at the time of forming the photoelectric conversion film 12 was set to 50° C.

Next, the dark currents (unit: mA) of the photoelectric conversion element A1 and the photoelectric conversion element B1 were measured. Specifically, the dark current was measured by applying a voltage to each element under conditions such that the external quantum efficiency at 540 nm was 65%.

The dependency on the substrate temperature during vapor deposition was evaluated according to the following evaluation criteria based on the numerical value (a relative value) obtained by Expression (A) below.

Practically, "A" or "B" is preferable, and "A" is more preferable.

The results are shown in Table 1.

Expression $(A)$=(dark current of photoelectric conversion element $B1$)/(dark current of photoelectric conversion element $A1$)

Evaluation Criteria

"A": a case where a relative value obtained by the above expression (A) is less than 1.2

"B": a case where the relative value obtained by the above expression (A) is 1.2 or more and less than 1.5

"C": a case where the relative value obtained by the above expression (A) is 1.5 or more and less than 3

"D": a case where the relative value obtained by the above expression (A) is 3 or more

Evaluation of Performance Change Rate Due to Mixing Ratio (Dependency of Photoelectric Conversion Efficiency on Composition Ratio)

Next, the change rate of the photoelectric conversion efficiency in a case where the mixing ratio with the n-type organic semiconductor was changed was evaluated.

In the production of the photoelectric conversion element A1 described above, the photoelectric conversion element C1 was produced by the same method except that the photoelectric conversion film 12 was changed to include the compound (D-1) and fullerene (C60) of 120 nm and 80 nm respectively in terms of a single layer. Also, in the production of the photoelectric conversion element A1 described above, the photoelectric conversion element D1 was produced by the same method except that the photoelectric conversion film 12 was changed to include the compound (D-1) and fullerene (C60) of 80 nm and 120 nm respectively in terms of a single layer.

Stated another way, three types of the photoelectric conversion elements (A1, C1, and D1) having different the composition ratios of the compound (D-1) and the n-type organic semiconductor in the photoelectric conversion film 12 (in other words, the content of the compound (D-1) in the photoelectric conversion film 12 is different) were prepared.

Next, the following photoelectric conversion efficiency was evaluated using the photoelectric conversion elements A1, C1, and D1. Specifically, a voltage was applied to each photoelectric conversion element so that the electric field strength was $1.0\times10^5$ V/cm, and the photoelectric conversion efficiency at 540 nm was measured.

The evaluation of the performance change rate due to the mixing ratio was evaluated according to the following evaluation criteria based on numerical values (the relative values) obtained by Expression (B) and Expression (C) below. Practically, "A" or "B" is preferable, and "A" is more preferable.

The results are shown in Table 1.

Expression $(B)$=(photoelectric conversion efficiency of photoelectric conversion element $C1$)/(photoelectric conversion efficiency of photoelectric conversion element $A1$)

Expression $(C)$=(photoelectric conversion efficiency of photoelectric conversion element $D1$)/(photoelectric conversion efficiency of photoelectric conversion element $A1$)

Evaluation Criteria

"A": a case where both the relative values obtained by Expression (B) and Expression (C) above are 0.95 or more and less than 1.05

"B": a case where one of the relative values obtained by Expression (B) and Expression (C) above is 0.95 or more and less than 1.05, and the other is 0.90 or more and less than 0.95, or 1.05 or more and less than 1.10

"C": a case where both the relative values obtained by Expression (B) and Expression (C) above are 0.90 or more and less than 0.95, or 1.05 or more and less than 1.10

"D": a case where at least any one of the relative value obtained by Expression (B) or Expression (C) above is less than 0.90 or 1.10 or more Examples 2 to 12 and Comparative Examples 1 to 4

As shown in Table 1, except that the compound (D-1) was changed to the compounds (D-2) to (D-12) and the compounds (R-1) to (R-4), respectively, various evaluations were performed according to the same procedure as in Example 1.

(1) as a photoelectric conversion material exhibited excellent production suitability (characteristics of less dependency on the substrate temperature during vapor deposition in forming a photoelectric conversion film and less dependency of the photoelectric conversion efficiency on the composition ratio).

From the comparison of Example 1, Example 3, Example 8, and Example 9, it was confirmed that in a case where the compound represented by Formula (1) is the compound represented by Formula (3) (preferably the compound represented by Formula (4)), the dependency of the photoelectric conversion efficiency on the composition ratio is smaller.

Further, from the comparison between Examples 1 to 7 and Examples 10 to 12, it was confirmed that in the compound represented by Formula (3) and the compound represented by Formula (4), in a case where $R^6$ to $R^9$ represent hydrogen atoms or aryl groups which may have a substituent (preferably, a case where $R^6$ to $R^9$ represent hydrogen atoms, or a case where $R^6$, $R^8$, and $R^9$ represent hydrogen atoms, and $R^7$ represents an aryl group which may have a substituent), the dependency on the substrate temperature during vapor deposition in the photoelectric conversion film formation is smaller.

TABLE 1

| | | Compound | | Driving confirmation | Evaluation Dependency on substrate temperature during vapor deposition | Dependency of photoelectric conversion efficiency on composition ratio |
|---|---|---|---|---|---|---|
| | Type | Skeleton | Types of $R^6$ to $R^9$ | | | |
| Example 1 | D-1 | Expression (3)/Expression (4) | All hydrogen atom | A | A | A |
| Example 2 | D-2 | Expression (3)/Expression (4) | All hydrogen atom | A | A | A |
| Example 3 | D-3 | Expression (3)/Expression (4) | All hydrogen atom | A | A | A |
| Example 4 | D-4 | Expression (3)/Expression (4) | $R^7$: Alkyl group $R^6$, $R^8$, $R^9$: Hydrogen atom | A | B | A |
| Example 5 | D-5 | Expression (3)/Expression (4) | $R^7$: Perfluoroalkyl group $R^6$, $R^8$, $R^9$: Hydrogen atom | A | B | A |
| Example 6 | D-6 | Expression (3)/Expression (4) | All hydrogen atom | A | A | A |
| Example 7 | D-7 | Expression (3)/Expression (4) | All hydrogen atom | A | A | A |
| Example 8 | D-8 | Expression (2) ($X^1$: sulfur atom) | All hydrogen atom | A | A | B |
| Example 9 | D-9 | Expression (2) ($X^1$: sulfur atom) | All hydrogen atom | A | A | B |
| Example 10 | D-10 | Expression (3)/Expression (4) | $R^7$: Alkyl-substituted aryl group $R^6$, $R^8$, $R^9$: Hydrogen atom | A | A | A |
| Example 11 | D-11 | Expression (3)/Expression (4) | $R^7$: Alkyl-substituted aryl group $R^6$, $R^8$, $R^9$: Hydrogen atom | A | A | A |
| Example 12 | D-12 | Expression (3)/Expression (4) | $R^7$: Alkyl-substituted aryl group $R^6$, $R^8$, $R^9$: Hydrogen atom | A | A | A |
| Comparative Example 1 | R-1 | | | A | C | C |
| Comparative Example 2 | R-2 | | | A | C | C |
| Comparative Example 3 | R-3 | | | A | D | D |
| Comparative Example 4 | R-4 | | | A | C | C |

From the results in Table 1, it was confirmed that the photoelectric conversion element in the embodiment of the invention containing the compound represented by Formula The production suitability (the characteristics of less dependency on the substrate temperature during vapor deposition in forming a photoelectric conversion film and less dependency of the photoelectric conversion efficiency on the composition ratio) of the photoelectric conversion elements of Comparative Examples 1 to 4 does not satisfy a desired requirements.

Production of Imaging Element

The same imaging element as shown in FIG. 3 was produced using the compounds (D-1) to (D-12).

That is, 30 nm of an amorphous TiN was formed into a film on a CMOS substrate by a sputtering method, and was used as the lower electrode through patterning such that each pixel was present on the photodiode (PD) on the CMOS substrate through photolithography, and then the imaging element was produced similarly to Examples 1 to 12 after the film formation of the electron blocking material. With the obtained imaging element, evaluation of production suitability (evaluation of dependency on the substrate temperature during vapor deposition in the photoelectric conversion film formation and evaluation of dependency of the photoelectric conversion efficiency on the composition ratio) was also performed in the same manner, and the result was obtained as in Table 1. From this, it was found that the photoelectric conversion element of the embodiment of the invention also exhibits excellent performance in the imaging element.

EXPLANATION OF REFERENCES 10a, 10b: photoelectric conversion element
11: conductive film (lower electrode)
12: photoelectric conversion film
15: transparent conductive film (upper electrode)
16A: electron blocking film
16B: positive hole blocking film
100: pixel separation type imaging element
101: substrate
102: insulating layer
103: connection electrode
104: pixel electrode (lower electrode)
105: connection unit
106: connection unit
107: photoelectric conversion film
108: counter electrode (upper electrode)
109: buffer layer
110: sealing layer
111: color filter (CF)
112: partition wall
113: light shielding layer
114: protective layer
115: counter electrode voltage supply unit
116: readout circuit
200: photoelectric conversion element (hybrid type photoelectric conversion element)
201: inorganic photoelectric conversion film
202: n-type well
203: p-type well
204: n-type well
205: p-type silicon substrate
207: insulating layer
208: pixel electrode
209: organic photoelectric conversion film
210: common electrode
211: protective film
212: electron blocking film

What is claimed is:
1. A photoelectric conversion element comprising:
a conductive film;
a photoelectric conversion film; and
a transparent conductive film, in this order,
wherein the photoelectric conversion film contains a compound represented by Formula (1) below,

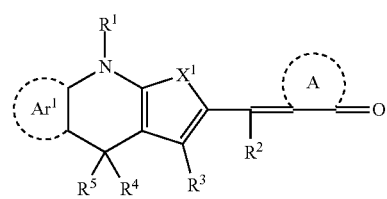

(1)

in Formula (1), $R^1$ represents an alkyl group which may have a substituent, $R^2$ to $R^5$ each independently represent a hydrogen atom or a substituent, $X^1$ represents a sulfur atom or $-R^{a1}C=CR^{a2}-$, $R^{a1}$ and $R^{a2}$ each independently represent a hydrogen atom or a substituent, $Ar^1$ represents a monocyclic aromatic ring containing at least two carbon atoms, which may have a substituent, A represents a ring containing at least two carbon atoms, which may have a substituent, and in Formula (1), the respective substituents may bond to each other to form a ring, provided that, in a case where a plurality of the substituents on the $Ar^1$ bond to each other to form a ring, the ring does not include an aromatic ring, and the compound represented by Formula (1) does not contain both an acidic group and a salt thereof.

2. The photoelectric conversion element according to claim 1,
wherein the compound represented by Formula (1) is a compound represented by Formula (2) below,

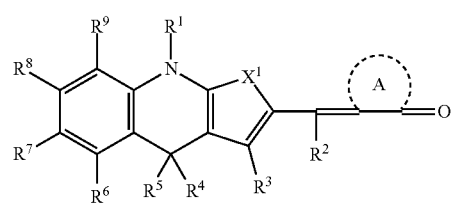

(2)

in Formula (2), $R^1$ represents an alkyl group which may have a substituent, $R^2$ to $R^9$ each independently represent a hydrogen atom or a substituent, $X^1$ represents a sulfur atom or $-R^{a1}C=CR^{a2}-$, $R^{a1}$ and $R^{a2}$ each independently represent a hydrogen atom or a substituent, A represents a ring containing at least two carbon atoms, which may have a substituent, and in Formula (2), the respective substituents may bond to each other to form a ring, provided that, in a case where $R^6$ and $R^7$, $R^7$ and $R^8$, and $R^8$ and $R^9$ bond to each other to form a ring, the ring does not include an aromatic ring, and the compound represented by Formula (2) does not contain both an acidic group and a salt thereof.

3. The photoelectric conversion element according to claim 2,
wherein the compound represented by Formula (2) is a compound represented by Formula (3) below,

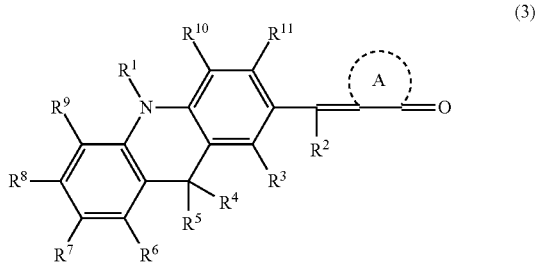

(3)

in Formula (3), $R^1$ represents an alkyl group which may have a substituent, $R^2$ to $R^{11}$ each independently represent a hydrogen atom or a substituent, A represents a ring containing at least two carbon atoms, which may have a substituent, and in Formula (3), the respective substituents may bond to each other to form a ring, provided that, in a case where $R^6$ and $R^7$, $R^7$ and $R^8$, and $R^8$ and $R^9$ bond to each other to form a ring, the ring does not include an aromatic ring, and the compound represented by Formula (3) does not contain both an acidic group and a salt thereof.

4. The photoelectric conversion element according to claim 3,
wherein the compound represented by Formula (3) is a compound represented by Formula (4) below,

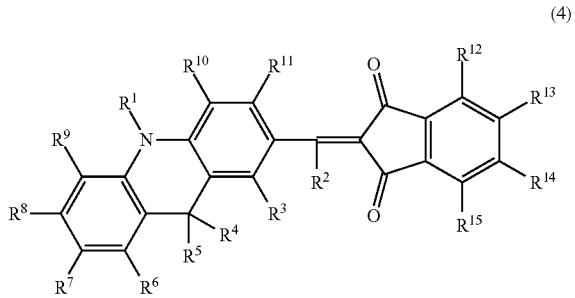

(4)

in Formula (4), $R^1$ represents an alkyl group which may have a substituent, $R^2$ to $R^{15}$ each independently represent a hydrogen atom or a substituent, and in Formula (4), the respective substituents may bond to each other to form a ring, provided that, in a case where $R^6$ and $R^7$, $R^7$ and $R^8$, and $R^8$ and $R^9$ bond to each other to form a ring, the ring does not include an aromatic ring, and the compound represented by Formula (4) does not contain both an acidic group and a salt thereof.

5. The photoelectric conversion element according to claim 1,
wherein the $R^4$ and the $R^5$ are alkyl groups which may have a substituent, or
the $R^4$ and $R^5$ bond to each other to form an alicyclic hydrocarbon ring which may have a substituent.

6. The photoelectric conversion element according to claim 1,
wherein the photoelectric conversion film further contains an n-type organic semiconductor and has a bulk hetero structure formed in a state where the compound represented by Formula (1) and the n-type organic semiconductor are mixed.

7. The photoelectric conversion element according to claim 1, further comprising one or more interlayers between the conductive film and the transparent conductive film, in addition to the photoelectric conversion film.

8. An optical sensor comprising the photoelectric conversion element according to claim 1.

9. An imaging element comprising the photoelectric conversion element according to claim 1.

10. The photoelectric conversion element according to claim 2,
wherein the $R^4$ and the $R^5$ are alkyl groups which may have a substituent, or
the $R^4$ and $R^5$ bond to each other to form an alicyclic hydrocarbon ring which may have a substituent.

11. The photoelectric conversion element according to claim 3,
wherein the $R^4$ and the $R^5$ are alkyl groups which may have a substituent, or
the $R^4$ and $R^5$ bond to each other to form an alicyclic hydrocarbon ring which may have a substituent.

12. The photoelectric conversion element according to claim 4,
wherein the $R^4$ and the $R^5$ are alkyl groups which may have a substituent, or
the $R^4$ and $R^5$ bond to each other to form an alicyclic hydrocarbon ring which may have a substituent.

13. The photoelectric conversion element according to claim 2,
wherein the photoelectric conversion film further contains an n-type organic semiconductor and has a bulk hetero structure formed in a state where the compound represented by Formula (1) and the n-type organic semiconductor are mixed.

14. The photoelectric conversion element according to claim 3,
wherein the photoelectric conversion film further contains an n-type organic semiconductor and has a bulk hetero structure formed in a state where the compound represented by Formula (1) and the n-type organic semiconductor are mixed.

15. The photoelectric conversion element according to claim 4,
wherein the photoelectric conversion film further contains an n-type organic semiconductor and has a bulk hetero structure formed in a state where the compound represented by Formula (1) and the n-type organic semiconductor are mixed.

16. The photoelectric conversion element according to claim 5,
wherein the photoelectric conversion film further contains an n-type organic semiconductor and has a bulk hetero structure formed in a state where the compound represented by Formula (1) and the n-type organic semiconductor are mixed.

17. The photoelectric conversion element according to claim 2, further comprising one or more interlayers between the conductive film and the transparent conductive film, in addition to the photoelectric conversion film.

18. The photoelectric conversion element according to claim 3, further comprising one or more interlayers between the conductive film and the transparent conductive film, in addition to the photoelectric conversion film.

19. The photoelectric conversion element according to claim 4, further comprising one or more interlayers between the conductive film and the transparent conductive film, in addition to the photoelectric conversion film.

20. The photoelectric conversion element according to claim 5, further comprising one or more interlayers between the conductive film and the transparent conductive film, in addition to the photoelectric conversion film.

\* \* \* \* \*